United States Patent
Holbrook

(10) Patent No.: US 11,273,269 B2
(45) Date of Patent: Mar. 15, 2022

(54) INSUFFLATION RETENTION DEVICE

(71) Applicant: BPENDO, LLC, Norman, OK (US)

(72) Inventor: Robert M. Holbrook, Norman, OK (US)

(73) Assignee: BPENDO, LLC, Norman, OK (US)

(*) Notice: Subject to any disclaimer, the term of this patent is extended or adjusted under 35 U.S.C. 154(b) by 0 days.

(21) Appl. No.: 15/976,885

(22) Filed: May 11, 2018

(65) Prior Publication Data

US 2018/0326165 A1 Nov. 15, 2018

Related U.S. Application Data

(60) Provisional application No. 62/505,095, filed on May 11, 2017.

(51) Int. Cl.
*A61M 13/00* (2006.01)
*A61B 17/34* (2006.01)

(52) U.S. Cl.
CPC ....... *A61M 13/003* (2013.01); *A61B 17/3423* (2013.01); *A61B 17/3462* (2013.01);
(Continued)

(58) Field of Classification Search
CPC .. A61M 13/003; A61M 13/00; A61M 13/006; A61M 2205/0216;
(Continued)

(56) References Cited

U.S. PATENT DOCUMENTS 3,154,077 A * 10/1964 Cannon ............ A61B 17/12099
604/101.05
3,745,992 A * 7/1973 Poirier .................. A61B 1/303
600/225
(Continued)

FOREIGN PATENT DOCUMENTS

JP  H0923560 A   1/1997
JP  2015062441 A  4/2015
(Continued)

OTHER PUBLICATIONS

Technology Status Evaluation Report: Methods of luminal distention for colonoscopy, Gastrointestinal Endoscopy, vol. 77, No. 4, 2013, pp. 519-525.
(Continued)

*Primary Examiner* — Brandy S Lee
*Assistant Examiner* — Hong-Van N Trinh
(74) *Attorney, Agent, or Firm* — Michael S. Young IP Law LLC; Michael S. Young

(57) ABSTRACT

A probe may be inserted into a body cavity to perform diagnostic intervention(s), therapeutic intervention(s), or both. The probe may be inserted through a body aperture that is naturally occurring or man-made, intentionally or by accident. The body aperture may form a seal encircling the probe so that insufflation retention material may be effectively retained in the body cavity so that an operator can perform the intervention(s). However, there may be leakage of the insufflation material. The insufflation retention device is configured to form an effective seal contactingly adjacent the body aperture and to provide a passageway for the introduction of the probe into the body cavity, such that a diagnostic intervention or therapeutic intervention or both may be performed.

29 Claims, 14 Drawing Sheets

(52) U.S. Cl.
CPC ............... *A61B 2017/3425* (2013.01); *A61B 2017/3429* (2013.01); *A61B 2017/3437* (2013.01); *A61B 2017/3441* (2013.01); *A61B 2017/3486* (2013.01); *A61M 2202/0208* (2013.01); *A61M 2202/0225* (2013.01); *A61M 2202/0468* (2013.01)

(58) Field of Classification Search
CPC .. A61M 2205/0222; A61M 2210/1064; A61M 29/00; A61M 29/02; A61M 25/10; A61M 25/1002; A61M 25/1011; A61M 2202/0208; A61M 2202/0225; A61M 2202/0468; A61B 1/31; A61B 17/3462; A61B 2017/3441; A61B 17/3423; A61B 2017/348; A61B 2017/3492; A61B 2017/3484; A61B 1/00; A61B 1/00082; A61B 1/00154; A61B 2017/3425; A61B 2017/3429; A61B 2017/3437; A61B 2017/3486; A61F 2/00; A61F 2/0004; A61F 2/0009; A61F 2/0013
See application file for complete search history.

(56) References Cited

U.S. PATENT DOCUMENTS

| | | | |
|---|---|---|---|
| 3,802,418 A | | 4/1974 | Clayton |
| 4,776,845 A * | | 10/1988 | Davis ................... A61B 1/31 |
| | | | 600/114 |
| 4,957,486 A | | 9/1990 | Davis |
| 4,984,564 A | | 1/1991 | Yuen |
| 5,836,048 A | | 11/1998 | Rossman et al. |
| 5,904,701 A | | 5/1999 | Daneshvar |
| 5,964,781 A * | | 10/1999 | Mollenauer ...... A61B 17/00234 |
| | | | 606/192 |
| 6,768,058 B2 * | | 7/2004 | Pallapothu .......... B60R 16/0222 |
| | | | 16/2.1 |
| 7,967,809 B2 | | 6/2011 | Jay-Robinson |
| 8,057,448 B2 | | 11/2011 | Williams et al. |
| 8,235,942 B2 | | 8/2012 | Frassica et al. |
| 8,419,695 B2 | | 4/2013 | Rauker et al. |
| 8,939,952 B2 * | | 1/2015 | Weig .................... A61F 2/0027 |
| | | | 604/355 |
| 8,979,884 B2 | | 3/2015 | Milsom et al. |
| 9,924,853 B2 | | 3/2018 | Milsom et al. |
| 9,986,893 B2 | | 6/2018 | Cornhill et al. |
| 10,149,601 B2 | | 12/2018 | Milsom et al. |
| 10,485,401 B2 | | 11/2019 | Cruz et al. |
| 2003/0208223 A1 | | 11/2003 | Kleiner |
| 2005/0165432 A1 * | | 7/2005 | Heinrich ............ A61B 17/3417 |
| | | | 606/167 |
| 2006/0020164 A1 | | 1/2006 | Butler et al. |
| 2006/0271095 A1 | | 11/2006 | Rauker et al. |
| 2007/0005086 A1 * | | 1/2007 | Gresham ............ A61B 17/3496 |
| | | | 606/167 |
| 2007/0213661 A1 * | | 9/2007 | Gobel .................... A61F 2/0013 |
| | | | 604/96.01 |
| 2008/0092901 A1 * | | 4/2008 | Kang ................ A61M 16/0493 |
| | | | 128/207.15 |
| 2009/0326490 A1 | | 12/2009 | McMichael et al. |
| 2010/0312066 A1 * | | 12/2010 | Cropper ............. A61B 17/3423 |
| | | | 600/207 |
| 2011/0218389 A1 | | 9/2011 | Gobel |
| 2014/0018625 A1 | | 1/2014 | Lal |
| 2014/0066953 A1 | | 3/2014 | Keating et al. |
| 2014/0296831 A1 | | 10/2014 | Gobel |
| 2019/0069761 A1 | | 3/2019 | Milsom et al. |

FOREIGN PATENT DOCUMENTS

| | | |
|---|---|---|
| WO | 9422357 A2 | 10/1994 |
| WO | WO2006126061 A1 | 11/2006 |
| WO | 2015123313 A1 | 8/2015 |
| WO | 2015164591 A1 | 10/2015 |

OTHER PUBLICATIONS

International Search Report dated Aug. 1, 2018, International Application No. PCT/US18/32373.
Flexi-Seal REF418000 package insert, package usage date through Oct. 1, 2021.
Flexi-Seal REF41800 webpage capture, last visited Dec. 13, 2018.
International Search Report, PCT/US 19/00024, dated Oct. 24, 2019, pp. 1-12.
Supplementary European Search Report N419691EP, dated Jan. 14, 2021.
Supplementary European Search Report N420603EP MPR, dated Dec. 3, 2021.

* cited by examiner

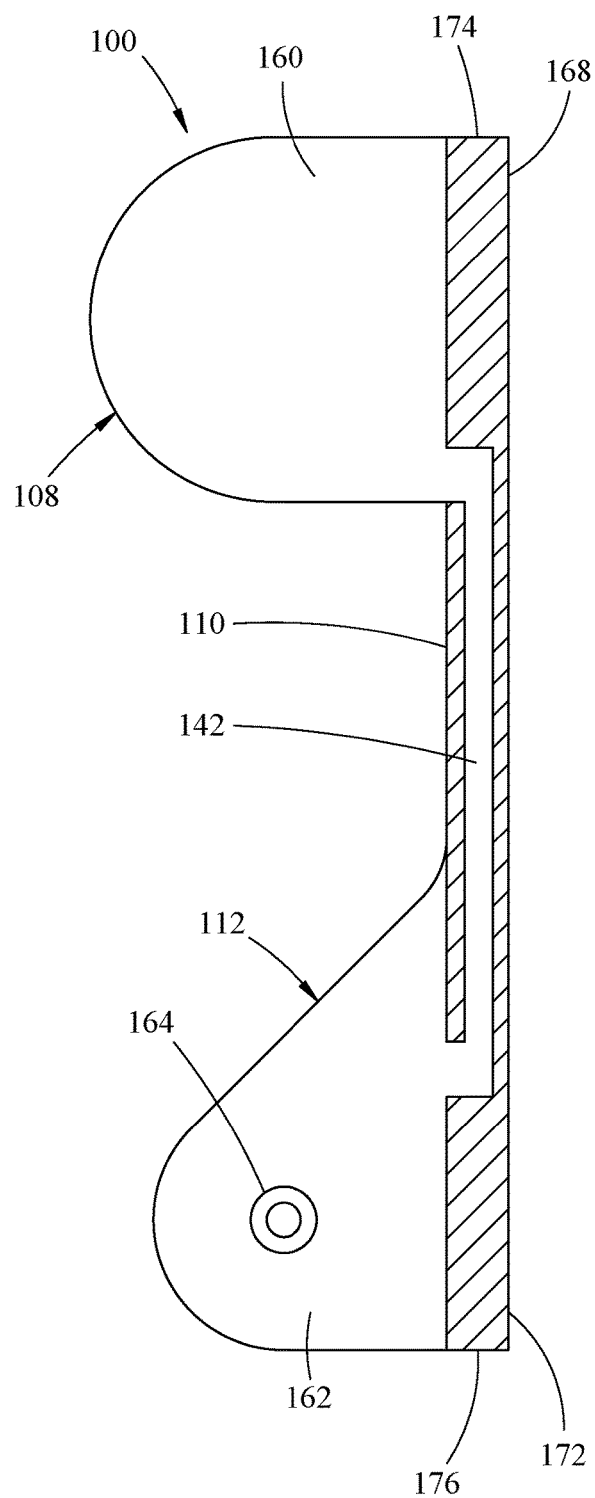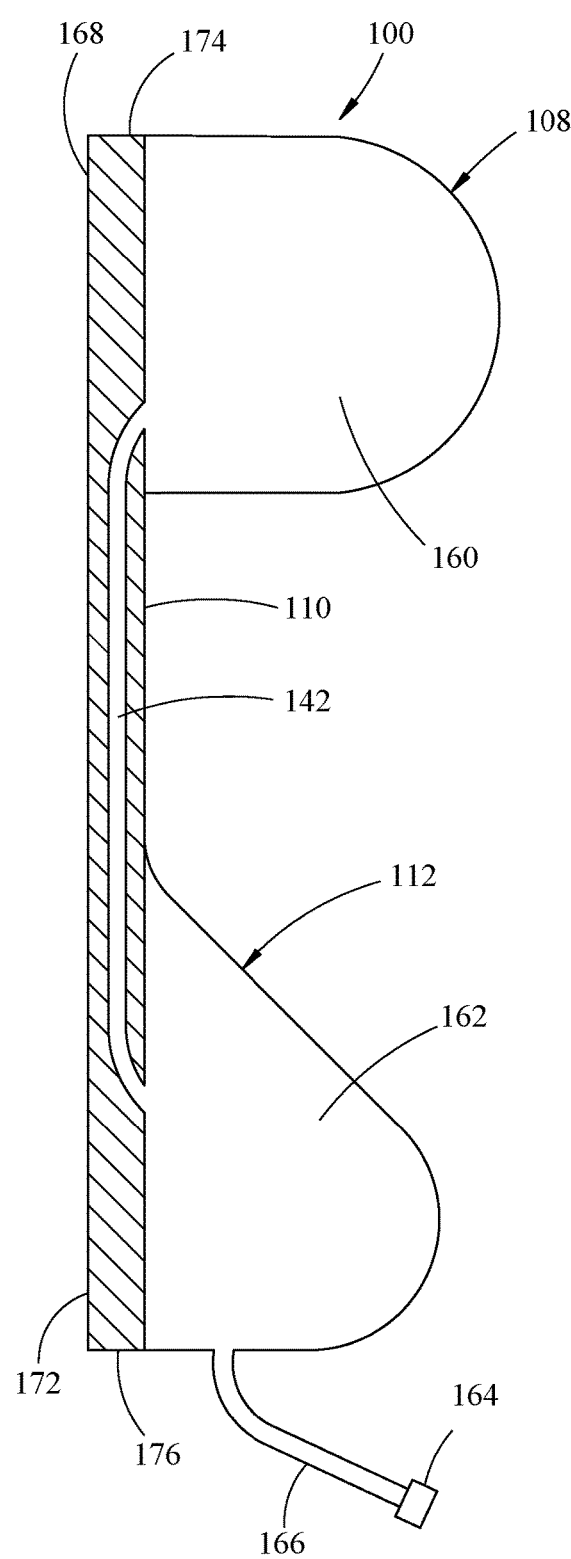
FIG. 5
FIG. 6

006
INSUFFLATION RETENTION DEVICE

CROSS-REFERENCE TO RELATED APPLICATIONS

The present application claims priority to U.S. Prov. Pat. App. No. 62/505,095 entitled Insufflation Retention Device, which was filed May 11, 2018 and with the present application. The U.S. Prov. Pat. App. No. 62/505,095 is hereby incorporated in its entirety into the present application.

SUMMARY

In accordance with various embodiments, a probe may be inserted into a body cavity to perform diagnostic intervention(s), therapeutic intervention(s), or both. The probe may be inserted through a body aperture that is naturally occurring or man-made, intentionally or by accident. The body aperture may form a seal encircling the probe so that insufflation retention material may be effectively retained in the body cavity so that an operator can perform the intervention(s). However, there may be leakage of the insufflation material. The insufflation retention device is configured to form an effective seal contactingly adjacent the body aperture and to provide a passageway for the introduction of the probe into the body cavity.

BRIEF DESCRIPTION OF THE DRAWINGS

FIG. 5 shows in partial cross-section view a midportion of the insufflation retention device extending as an internal buttress portion and an opposing, external buttress portion in accordance with various embodiments.

FIG. 6 shows in partial cross-section view a midportion of the insufflation retention device extending as an internal buttress portion and an opposing, external buttress portion in accordance with various embodiments.

DETAILED DESCRIPTION

There are technologies that allow operators to introduce a probe, e.g., a medical scope, into a body cavity for diagnostic intervention or therapeutic intervention or both. When the probe is introduced, the body cavity may need to be expanded for the operator to perform the intervention(s). Using an insufflation technique, the operator may introduce an insufflation material to expand the body cavity, so the operator may have more room to work and better visibility in the body cavity to perform the intervention(s). E.g., see *Technology Status Evaluation Report: Methods of luminal distension for colonoscopy*, Gastrointestinal Endoscopy, Volume 77, No. 4, 2013, pages 519-525, which is incorporated by reference in its entirety. The insufflation material may be air, carbon dioxide, water, or other suitable materials.

The operator may start with the probe outside a body, and the operator may advance the probe through tissue of the body to introduce the probe into a cavity of the body, i.e., the body cavity. The probe may be advanced through the tissue via an aperture of the body, i.e., the body aperture, that is a naturally occurring orifice, e.g., an anus, or a wound, e.g., a surgical incision or a traumatic injury. The body aperture may have elasticity that allows the body aperture to recover its size and shape after any deformation from the probe being advanced through the body aperture into the body cavity to effectively seal the outside of the body from the body cavity. Thereafter, the insufflation material introduced into the body cavity may be retained in the body cavity to help promote expansion of the body cavity when the outside of the body is effectively sealed from the body cavity to permit the operator to perform the intervention(s).

However, the insufflation material may not be effectively retained in the body cavity in some instances. For example, the body aperture or nearby structures may have a congenital malformation or may have suffered structural injury such as from scar tissue formation after abscess formation, surgical trauma, giving birth related injury, etc. that inhibits the body aperture from forming an effective seal with the probe.

If the insufflation material is not effectively retained, then the operator will not have time and room to work or visibility to operate in the body cavity. For example, the probe, such as an endoscope, may be introduced into the body cavity, such as a rectum and a large intestine, through the body aperture, such as the anus, and the elasticity of the body aperture may not effectively form a seal contactingly adjacent the probe to promote retention of the insufflation material in the body cavity. As will be described in further detail, this disclosure describes an insufflation retention device that promotes retention of the insufflation material in the body cavity.

Figure 1:
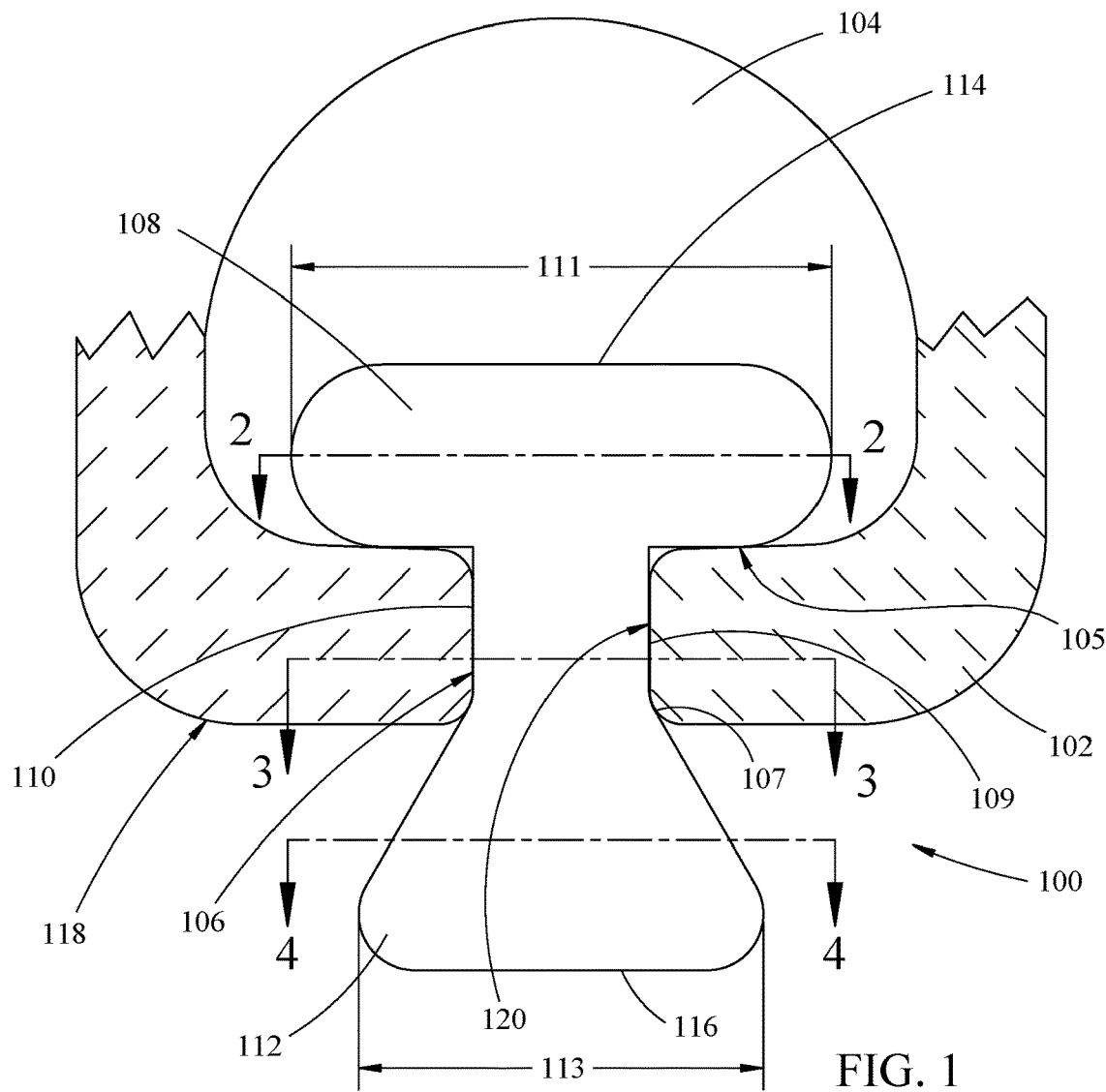
FIG. 1 shows in partial cross-section view an insufflation retention device through a body aperture and in a body cavity in accordance with various embodiments.

FIG. 1 shows an insufflation retention device (also known herein as IRD 100) that has been advanced from outside of a body 102 into a body cavity 104 through a body aperture 106, also known as an orifice. The IRD 100 may generally include an internal buttress 108, a midportion 110, and an external buttress 112. The internal buttress 108 is at a first end 114 of the IRD 100 and the external buttress 112 is at an opposing, second end 116 of the IRD 100 with the midportion 110 therebetween. In other words, the midportion 110 is disposed between the internal buttress 108 and the external buttress 112.

As shown in FIG. 1, a width 111 of the internal buttress 108 may be substantially greater than a width 113 of the external buttress 112. Alternatively, the width 111 of the internal buttress 108 may be substantially equal to the width 113 of the external buttress 112, as shown in later figures. Furthermore, the width 111 of the internal buttress 108 may be substantially less than the width 113 of the external buttress 112, as shown in later figures, also. The width 111 of the internal buttress 108 may be substantially parallel to the width 113 of the external buttress 112.

The internal buttress 108 may be configured to have an unexpanded configuration so that an operator may introduce the IRD 100 through the body aperture 106 into the body cavity 104. The unexpanded configuration of the internal buttress 108 may be smaller than an expanded configuration of the internal buttress 108 shown in FIG. 1. The unexpanded configuration of the internal buttress 108 is configured to facilitate entry of the IRD 100 from an exterior 118 of the body 102. In other words, in a contracted state the internal buttress 108 may be configured for insertion through the body aperture 106 of the body 102 into the body cavity 104 of the body 102.

The expanded configuration of the internal buttress 108 is configured to prevent the IRD 100 from being removed from the body cavity 104. If the IRD 100 moved towards the exterior 118 of the body 102, then the expanded configuration of the internal buttress 108 would contactingly engage the body cavity 104 or the body aperture 106 or both to prevent the IRD 100 from being removed from the body cavity 104. In other words, in the expanded state the internal buttress 108 may be configured to inhibit removal of the internal buttress 108 from the body cavity 104 through the body aperture 106.

The internal buttress 108 in an unexpanded configuration or contracted state may be increased in size to the expanded configuration or state through introduction of an expansion material into an internal cavity of the internal buttress 108 supplied by a source. The expansion material may be broadly considered to be a fluid. Examples of the expansion material may be a liquid e.g., water, and a gas e.g., oxygen, air, compressed air, carbon dioxide, by way of example and not limitation.

The internal buttress 108 may be configured to form a body internal buttress seal 105 between the body cavity 104 and the internal buttress 108. The internal buttress 108 is shown generally as a doughnut shape; however, other shapes are contemplated depending on the need of the operator in view of the body 102 of a patient. The shape of the internal buttress 108 may be chosen to be a predetermined shape to effectively form the body internal buttress seal 105 between the body 102 and the internal buttress 108. Effectiveness of the body internal buttress seal 105 occurs when insufflation material is retained in the body cavity 104 so that the operator can perform the intervention(s) and the operator will have time and room to work or visibility to operate in the body cavity 104.

The external buttress 112 may be considered to have an unexpanded configuration or contracted state, also. However, the unexpanded configuration of the external buttress 112 is not required. The reason that the unexpanded configuration of the external buttress 112 is not required is that the external buttress 112 is configured to prevent the IRD 100 from being introduced into the body cavity 104. For example, the external buttress 112 may have the unexpanded configuration that is not configured to prevent introduction of the IRD 100 into the body cavity 104. In this example, a user or operator could then transform or transition the unexpanded configuration of the external buttress 112 into the expanded configuration of the external buttress 112 to prevent the IRD 100 from being introduced into the body cavity 104. In other words, the external buttress 112 may be configured to inhibit advancement of the external buttress 112 through the body aperture 106 into the body cavity 104.

As with the internal buttress 108, the external buttress 112 in an unexpanded configuration may be increased in size to the expanded configuration or state through introduction of an expansion material into an internal cavity of the external buttress 112 supplied by a source. The expansion material may again be broadly considered to be a fluid. The expansion material used to expand the internal buttress 108 and the external buttress 112 may be the same or different in any given situation.

However, the external buttress 112 need not have a smaller or unexpanded configuration, because the external buttress 112 does not need to be introduced through the body aperture 106. Therefore, the external buttress 112 may be of a size and configuration that is substantially the same before and after introduction of the IRD 100 into the body 102, and the external buttress 112 may be of a size and configuration that is substantially the same before, during, and after use of the IRD 100 in the body 102. However, for other practical considerations, it may be convenient for the external buttress 112 to have a smaller unexpanded configuration. For example, the external buttress 112 in the unexpanded configuration may more easily fit into a medical kit or packaging.

The external buttress 112 may be configured to form a body external buttress seal 107 between the body 102 and the external buttress 112. The external buttress 112 is shown generally as a cone shape; however, other shapes are contemplated depending on the need of the operator in view of the body 102 of the patient. The shape of the external buttress 112 may be chosen to be a predetermined shape to effectively form the body external buttress seal 107 between the body 102 and the external buttress 112. Effectiveness of the body external buttress seal 107 occurs when insufflation material is retained in the body cavity 104 so that the operator can perform the intervention(s) and the operator will have time and room to work or visibility to operate in the body cavity 104.

The midportion 110 is configured to couple the internal buttress 108 to the external buttress 112. The midportion 110 is configured to contactingly engage a wall 120 of the body aperture 106.

The midportion may be configured to form a body midportion seal 109 between the body aperture 106 and the midportion 110. The midportion 110 is generally shown as a cylinder; however, other shapes are contemplated depending on the need of the operator in view of the body 102 of the patient. The shape of the midportion 110 may be chosen to be a predetermined shape to effectively form the body midportion seal 109 between the body 102 and the midportion 110. Effectiveness of the body midportion seal 109 occurs when insufflation material is retained in the body cavity 104 so that the operator can perform the intervention(s) and the operator will have time and room to work or visibility to operate in the body cavity 104.

Figure 2:
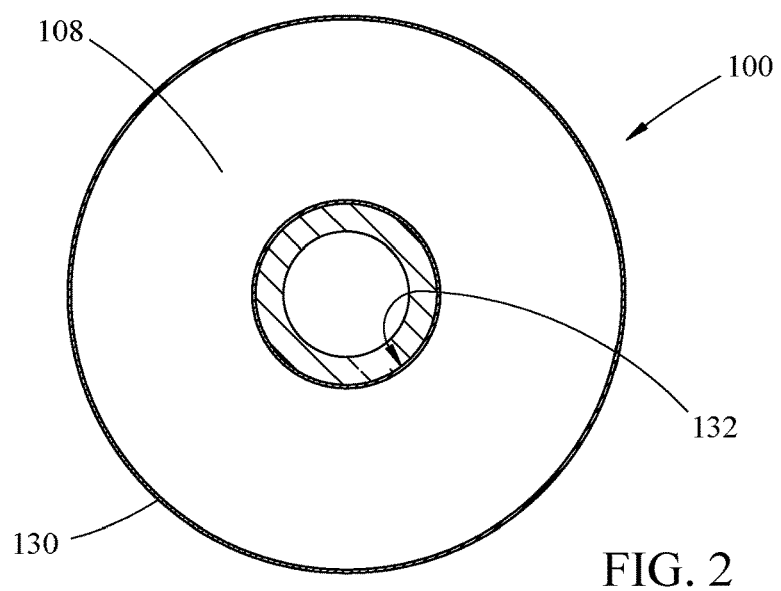
FIG. 2 shows in cross-section view the insufflation retention device of FIG. 1 in accordance with various embodiments.

FIG. 2 shows in cross-section the internal buttress of the IRD 100 of the embodiment shown in FIG. 1. An exterior periphery 130 of the internal buttress 108 may be configured to be expandable from the unexpanded configuration to the expanded configuration shown. An interior periphery 132 of the internal buttress 108 may be configured to be relatively rigid in comparison to the exterior periphery 130. This relatively rigidity of the interior periphery 132 of the internal buttress 108 may help the IRD 100 maintain its configuration and size when the probe is introduced into the IRD 100 and the probe moved back and forth, and in rotation within the IRD 100 when the operator performs the intervention(s).

Figure 3:
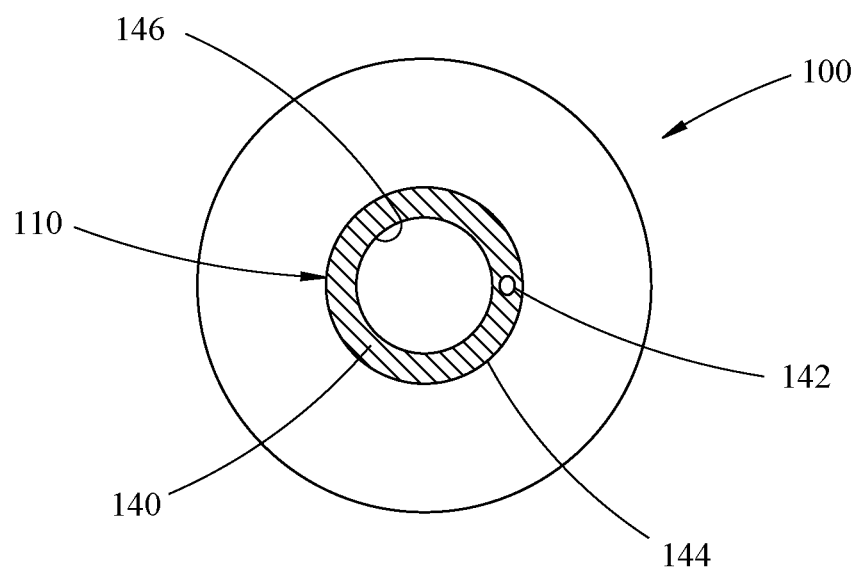
FIG. 3 shows in cross-section view the insufflation retention device of FIG. 1 in accordance with various embodiments.

FIG. 3 shows in cross-section the midportion of the IRD 100 of the embodiment shown in FIG. 1. Within a body 140 of the midportion 110, there may be an expansion material conduit 142 that may be used by the operator to introduce the expansion material into the internal cavity of the internal buttress 108. As can be seen, an exterior surface 144 of the midportion 110 may be substantially circular so that the IRD 100 may be relatively free to rotate clockwise or counterclockwise within the body aperture 106 as the operator inserts the IRD 100 into the body aperture 106, performs the intervention(s), or removes the IRD 100 from the body aperture 106. Likewise, an interior surface 146 of the midportion 110 may be substantially circular so that the IRD 100 may be relatively free to rotate clockwise or counterclockwise about the probe as the operator inserts the probe into the IRD 100, performs the intervention(s), removes the probe from the IRD 100, or attaches the IRD 100 to the probe. The exterior surface 144 of the midportion may be substantially parallel the interior surface 146 of the midportion. In other words, the midportion 110 may be a cylinder.

The interior surface 146 of the midportion 110 may be considered a sleeve that encircles the probe when the midportion 110 is in use. As shown, the sleeve may be substantially circular and disposed symmetrically within the body 140 of the midportion 110. Alternatively, the sleeve may be disposed asymmetrically within the body 140 of the midportion 110.

Figure 4:
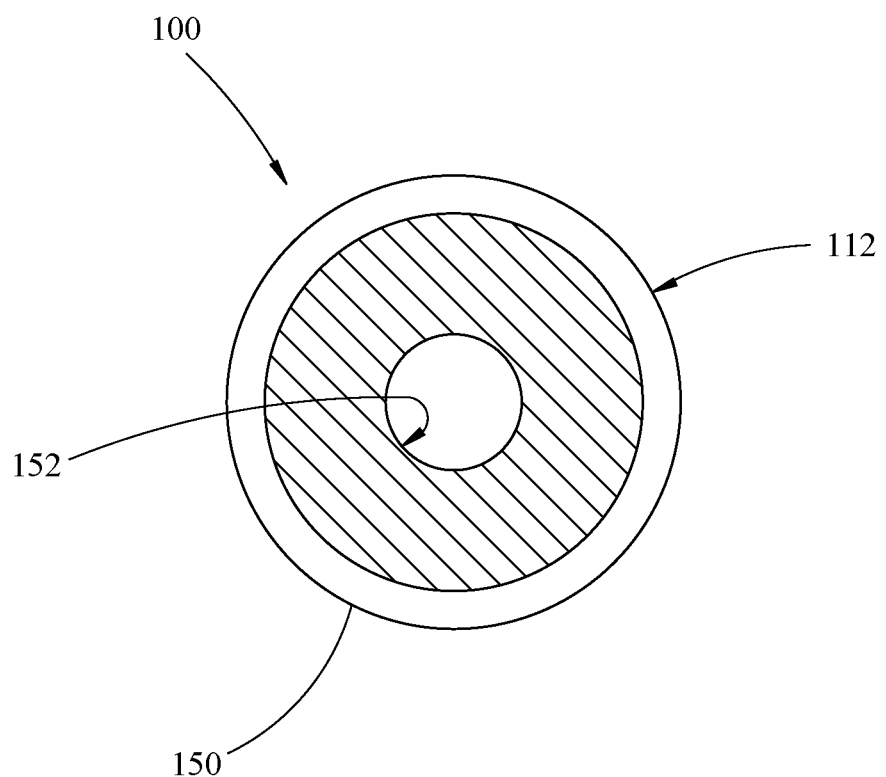
FIG. 4 shows in cross-section view the insufflation retention device of FIG. 1 in accordance with various embodiments.

FIG. 4 shows in cross-section the external buttress 112 of the IRD 100 of the embodiment shown in FIG. 1. An exterior periphery 150 of the external buttress 112 may be configured to be expandable from the unexpanded configuration to the expanded configuration. An interior surface 152 of the external buttress 112 may be configured to be relatively rigid in comparison to the exterior periphery 150. This relatively rigidity of the interior surface 152 of the external buttress may help the IRD 100 maintain its configuration so that the probe may be introduced into the IRD 100 and the probe moved back and forth, and in rotation within the IRD 100 when the operator performs the intervention(s).

The IRD 100 may be made of one or more biologically compatible materials. The biocompatible material may be a polymer, such as silicone or latex. The same polymer may be used for the internal buttress 108 and the external buttress 112 or different polymers may be used for the internal buttress 108 and the external buttress 112. The same polymer may be used for the midportion 110 as is used for the internal buttress 108 and the external buttress 112 or different polymers may be used for the midportion 110, the internal buttress 108, and the external buttress 112. The midportion 110 may be formed of one piece with the internal buttress 108 and the external buttress 112, or the midportion 110 may be formed of a different piece from the internal buttress 108 and the external buttress 112. The internal buttress 108 and the external buttress 112 may be formed of different pieces, also. If different pieces are used to the form the IRD 100, then laser welding, etc. may be used to the join the pieces.

FIG. 5 shows in cross-section an embodiment of the IRD 100 in which an internal cavity 160 of the internal buttress 108 is in fluid communication with an internal cavity an internal cavity of the external buttress of the external buttress 112 through the expansion material conduit 142 of the midportion 110. The expanded state is shown. An input valve 164 for the expansion material is shown coupled to the external buttress 112. The operator introduces the expansion material through the input valve 164 into the internal cavity 162 of the external buttress 112, the expansion material conduit 142 of the midportion 110, and the internal cavity 160 of the internal buttress 108 using a gas line, a syringe, or other suitable source of the expansion material.

FIG. 6 shows in cross-section another embodiment of the IRD 100 in which the internal cavity 160 of the internal buttress 108 is in fluid communication with the internal cavity 162 of the external buttress 112 through the expansion material conduit 142 of the midportion 110. The expanded state is shown. The input valve 164 for the expansion material is shown coupled to the external buttress 112 through an expansion material line 166 coupled to the external buttress 112. The expansion material line 166 may be rigid, flexible, or some combination of flexible and rigid. When flexible, the expansion material line 166 may assume any suitable orientation and orientation during use. When rigid, the expansion material line may maintain a predetermined orientation and configuration before, during, and after use. The operator introduces the expansion material through the input valve 164 into the expansion material line 166, the internal cavity 162 of the external buttress 112, the expansion material conduit 142 of the midportion 110, and the internal cavity 160 of the internal buttress 108.

FIG. 5 and FIG. 6 show the midportion 110 extending as an internal buttress portion 168 and an opposing, external buttress portion 172. The internal buttress 108 is part of the internal buttress portion 168, and the external buttress 112 is part of the opposing, external buttress portion 172. The internal buttress 108 may extend substantially short of, approximately even with, or substantially beyond a first end 174 of the internal buttress portion 168. The internal buttress 108 is shown approximately even with the first end 174 of the internal buttress portion 168. The external buttress 112 extend substantially short of, approximately even with, or substantially beyond a second end 176 of the external buttress portion 172. The external buttress 112 is shown approximately even with the second end 176 of the external buttress portion 172.

The expansion material conduit 142 of the midportion 110 may take any shape. FIG. 5 shows the expansion material conduit 142 starts at substantially right angles to the internal buttress 108 and the external buttress 112, while FIG. 6 shows the expansion material conduit 142 starts at substantially curvilinear orientation to the internal buttress 108 and the external buttress 112. Further, one or more pressure release valves in the IRD 100 may be configured to control when expansion of the external buttress 112 and the internal buttress 108 occur in relation to introduction of the expansion material. The pressure release valves may be of any suitable construction and are not shown.

Figure 7:
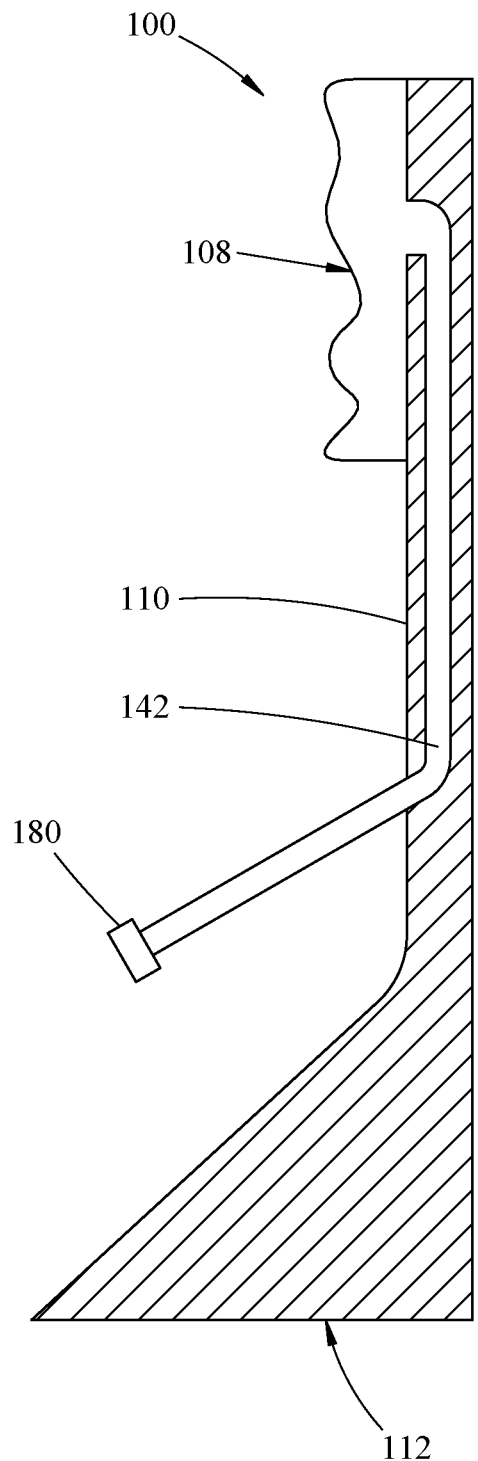
FIG. 7 shows in partial cross-section view an internal buttress input valve in fluid communication with an expansion material conduit in accordance with various embodiments.

FIG. 7 shows in cross-section another embodiment of the IRD 100 in which an internal buttress input valve 180 is in fluid communication with the expansion material conduit 142 of the midportion 110 to the internal buttress 108, while the external buttress 112 is not in fluid communication with the internal buttress input valve 180. The internal buttress 108 is shown in the unexpanded state. Of course, the internal buttress input valve 180 may be in direct fluid communication with the internal buttress 108 without the intervening expansion material conduit 142, which is not shown.

Figure 8:
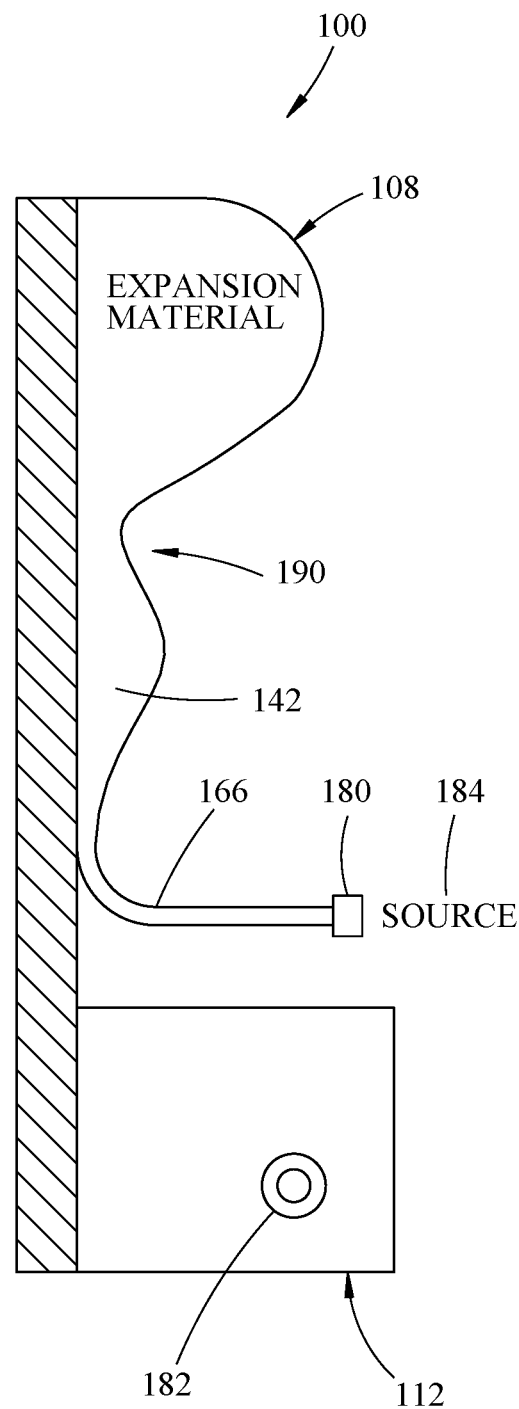
FIG. 8 shows in partial cross-section view an internal buttress input valve in fluid communication with an expansion material conduit and in external buttress with a separate external buttress input valve in accordance with various embodiments.

FIG. 8 shows in cross-section another embodiment of the IRD 100 in which the internal buttress input valve 180 through the expansion material line 166 is in fluid communication with the expansion material conduit 142 to expand the internal buttress 108 via introduction of the expansion material. Further, an external buttress input valve 182 is in fluid communication with the external buttress 112 to expand the external buttress 112 via introduction of the expansion material. In this embodiment of the IRD 100, the internal buttress input valve 180 and the external buttress input valve 182 may be independently operated by the operator or user to expand and contract the internal buttress 108 and expand and contract the external buttress 112 through introduction of the expansion material and removal of the expansion material via the internal buttress input valve 180 and the external buttress input valve 182. The internal buttress 108 is shown expanded by the expansion material supplied by an expansion material source 184.

The external buttress 112 is shown to have a rectangular shape as opposed to other buttress shapes previously shown with donut shape, conical shape, etc. Any suitable shape may be used for the internal buttress 108 or the external buttress 112.

In addition, the midportion 110 may have an external surface 190 that is not substantially flat. In other embodiments, the external surface 190 of the midportion 110 may be substantially flat. In this embodiment shown in FIG. 8, the external surface 190 of the midportion 110 is contoured, which is not substantially flat. The contour may be chosen by the operator based on anatomy of the body aperture 106 (see FIG. 1) and other features. The contour may help the IRD 100 achieve and maintain an effective seal for retention of the insufflation material. The contour shape and size may be responsive to absence or presence of the expansion material. As shown in FIG. 8, the contour may have the expansion material introduced through the expansion material line 166 that supplies the expansion material to the internal buttress 108. Of course, the contour may have the expansion material introduced through an expansion material line that is different and independent from the expansion material line 166 that supplies the expansion material to the internal buttress 108.

Besides going from a contracted or unexpanded state with less of the expansion material to the expanded state with more of the expansion material, the midportion 110 generally and the contour, as a specific example that is not limiting, may be substantially rigid. In an embodiment with the substantially rigid contour, the midportion 110 does not substantially deform during use of the IRD 100 from the orientation and configuration with respect to the IRD 100 before or after use of the IRD 100.

Figure 9:
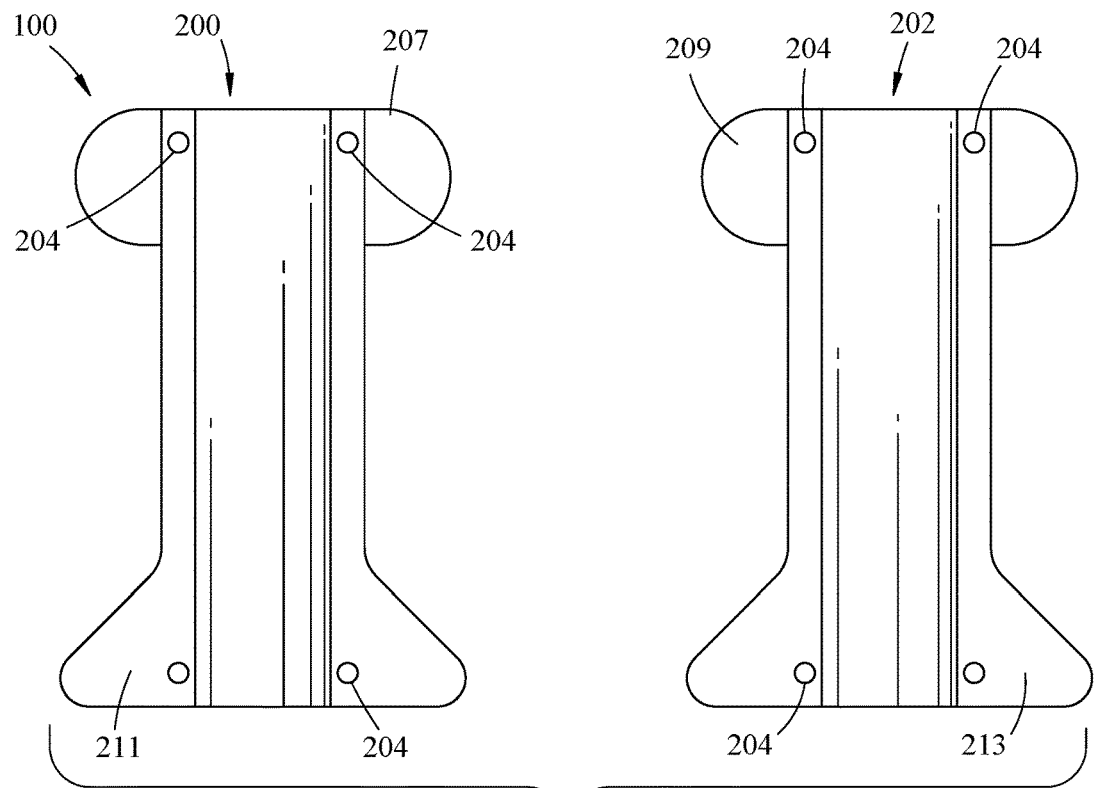
FIG. 9 shows in plan view a first body component and a second body component in accordance with various embodiments.

FIG. 9 shows another embodiment of the IRD 100. In this embodiment, the IRD 100 has a first body component 200 and a second body component 202. The first body component 200 is configured to be coupled to the second body component 202 to form the IRD 100 that is operational for use. The operator may wish to use such a two-body component system when the probe is already in the body aperture 106 or in both the body aperture 106 and the body cavity 104 (see FIG. 1). When the probe is in this position in the body aperture 106 or the body cavity 104, the operator may not be able to insert the probe into and through the IRD 100 or slide the IRD 100 over the probe. On the other hand, the operator will be able to couple the first body component 200 to the second body component 202 around the probe that remains in position in the body aperture 106 or in both the body aperture 106 and the body cavity 104. The first body component 200 may be coupled to the second body component 202 via one or more pairs of fasteners 204 of any suitable type, such as but not limited to snaps, clips, etc. Of course, this embodiment may also be used before the probe is in the body aperture 106 or the body cavity 104 or both.

As shown in this embodiment, the first body component 200 and the second body component 202 may have substantially parallel walls that are configured to effectively form a sleeve that provides a passageway for the probe when the first body component 200 may be coupled to the second body component 202. In this embodiment, a first internal buttress component 207 and a second internal buttress component 209 may be supplied with the expansion material via different introductions of the expansion material. In other words, the first internal buttress component 207 and the second internal buttress component 209 may not be in fluid communication.

Similarly, a first external buttress component 211 and a second external buttress component 213 may be supplied with the expansion material via different introductions of the expansion material, because the first external buttress component 211 and the second external buttress component 213 may not be in fluid communication. In this embodiment with the first body component 200 and the second body component 202, it may not be convenient to have the buttress components in fluid communication. Of course, one or more of the various buttress components may be in fluid communication, which is not shown.

Figure 10:
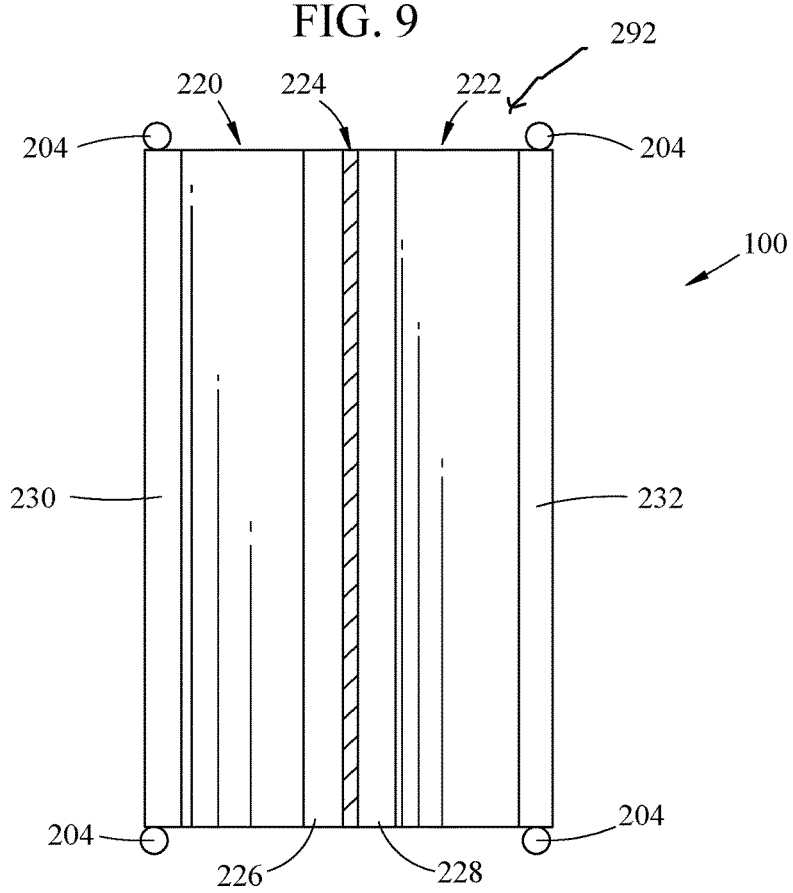
FIG. 10 shows in plan view a first body portion coupled to a second body portion via a hinge or pivot portion in accordance with various embodiments.

FIG. 10 shows another embodiment of the IRD 100. In this embodiment, a first body portion 220 is coupled to a second body portion 222 via a hinge portion 224 or flexible member at a first hinged side 226 of the first body portion 220 and a second hinged side 228 of the second body portion 222. The hinge portion 224 may be configured to allow the operator to take the IRD 100 from an open configuration with the seam 292 as shown in FIG. 10 to the closed configuration, not shown, with one-handed operation. One or more pairs of fasteners 204 may couple a first open edge 230 of the first body portion 220 to a second open edge 232 of the second body portion 222. The fasteners 204 may extend beyond the first body portion 220 and the second body portion 222 as shown in FIG. 10 or be within the perimeter of the first body component 200 and the second body component 202 as shown in FIG. 9.

In configuration shown in FIG. 10, it may be convenient for the internal buttress, not shown, to be in fluid communication encircling the first body portion 220 and the second body portion 222, in other words substantially the entire body portion, as present in some of the other embodiments. Further, it may be convenient for the external buttress, not shown, to be in fluid communication substantially encircling the first body portion 220 and the second body portion 222, as present in some of the other embodiments. The internal buttress 108 and the external buttress 112 are not shown in FIG. 10 for simplicity and would be understood to be on a surface of the IRD 100 in back of the view shown.

Figure 11:
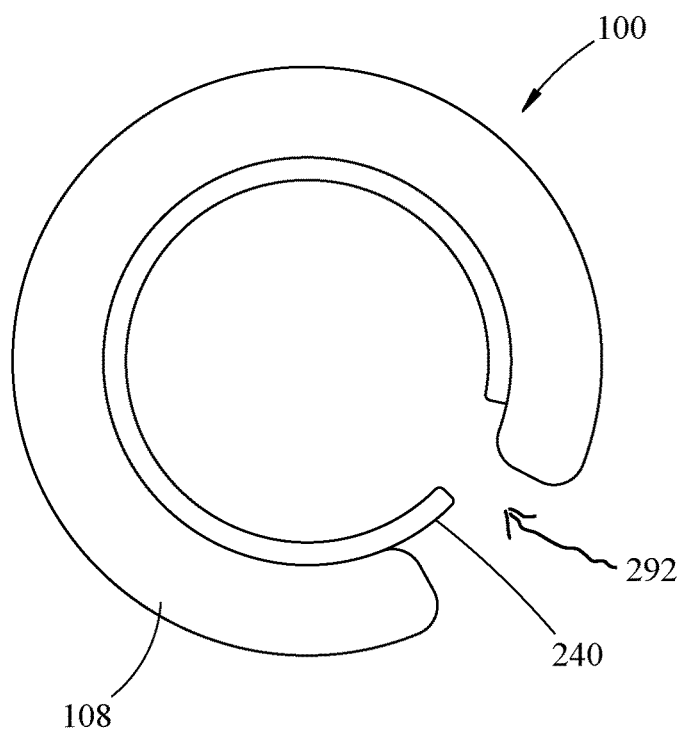
FIG. 11 shows in an end view an internal buttress coupled to a body portion in an open state that is biased to a closed state in accordance with various embodiments.
Figure 12:
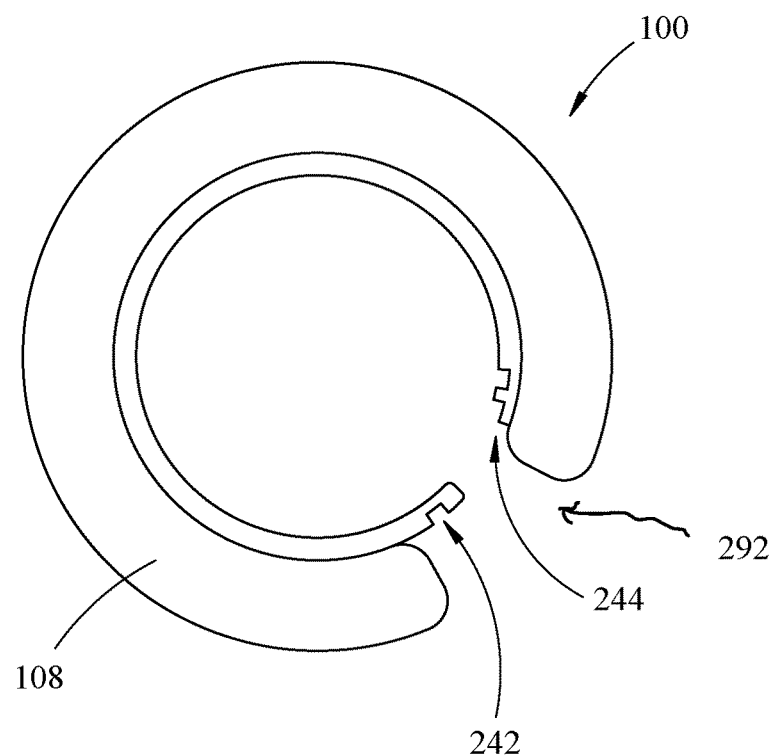
FIG. 12 shows in an end view internal buttress coupled to a body portion in an open state that is biased to a closed state with fasteners on the body portion in accordance with various embodiments.

FIGS. 11-12 show a cross-section through the internal buttress 108 in another embodiment of the IRD 100. In these embodiments, the internal buttress 108 may be coupled to an internal buttress body portion 240 via laser welding, adhesive, or other suitable means. Or the internal buttress 108 may be of one material with the internal buttress body portion 240. The internal buttress body portion 240 may have a bias to a closed state to form the sleeve that is sized and dimensioned to fit around the probe it will be used by the operator. The internal buttress body portion 240 is shown in the open state in FIG. 11 with a seam 292. The operator can position the IRD 100 around a probe when the internal buttress body portion 240 is in the open state when the IRD 100 is in the body cavity 104, the body aperture 106 or both, or when the IRD 100 is not in the body cavity 104, the body aperture 106 or both (see FIG. 1). Further, FIG. 12 shows the internal buttress body portion 240 with a first fastener 242 and a second fastener 244 in the open configuration to show the seam 292. The first fastener 242 is configured to be coupled to the second fastener 244 to form the sleeve that is sized and dimensioned to fit around a probe.

In addition, the internal buttress 108 may overlap the body portion 240 as shown to help form an effective seal for retention of the insufflation material. Alternatively, the internal buttress 108 may not overlap the internal buttress body portion 240, as not shown, and still achieve an effective seal for retention of the insufflation material.

Similarly, the external buttress may overlap or not overlap an analogous external buttress body portion to form an effective seal for retention of the insufflation material, which is not shown.

The apparatus may include an internal buttress configured to inhibit removal of the internal buttress from a body cavity through a body aperture of a body. An external buttress may be coupled to the internal buttress. The external buttress may be configured to inhibit entry of the external buttress into the body cavity through the body aperture. A passageway may extend through the internal buttress and the external buttress that is configured for passage of a probe into contacting engagement with the body cavity. The internal buttress in an expanded state may be configured to inhibit removal of the internal buttress from the body cavity through the body aperture, and the internal buttress in an unexpanded state may be configured to promote entry of the internal buttress into the body cavity through the body aperture. Alternatively, the internal buttress may be expanded with insertion of an expansion material to inhibit removal of the internal buttress from the body cavity through the body aperture, and the internal buttress may be contracted with removal of the expansion material to facilitate removal of the internal buttress from the body cavity through the body aperture.

Figure 13:
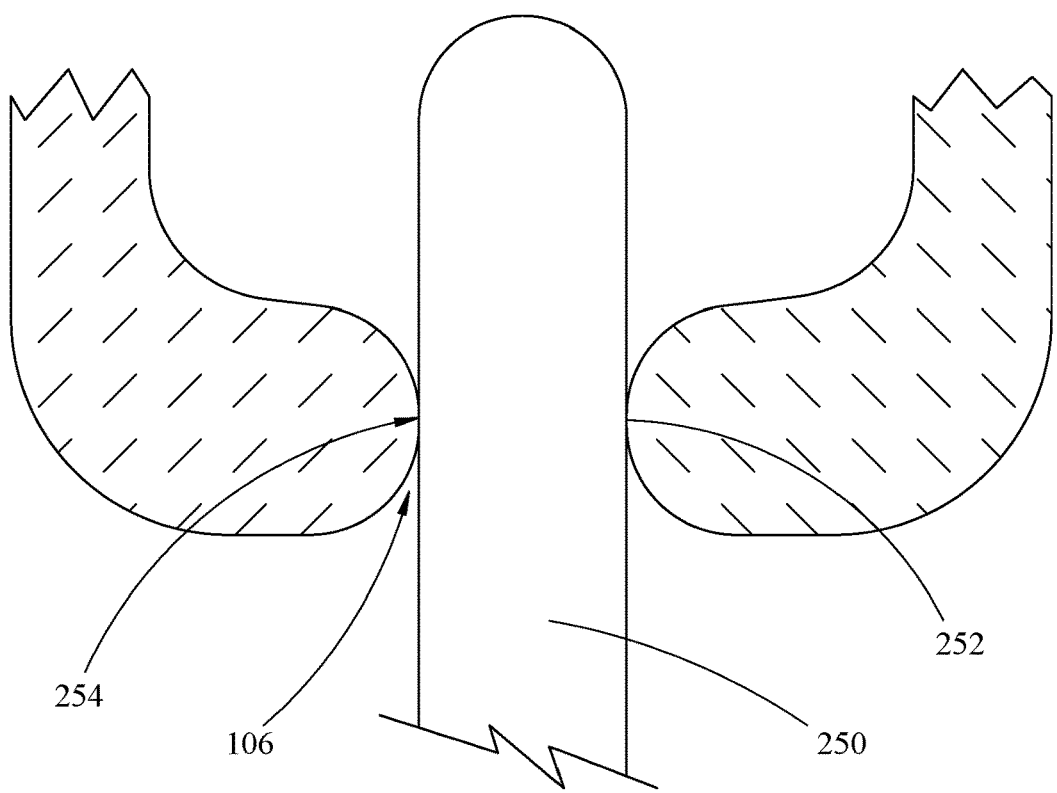
FIG. 13 shows in partial cross-section view a probe through a body aperture in accordance with various embodiments.
Figure 14:
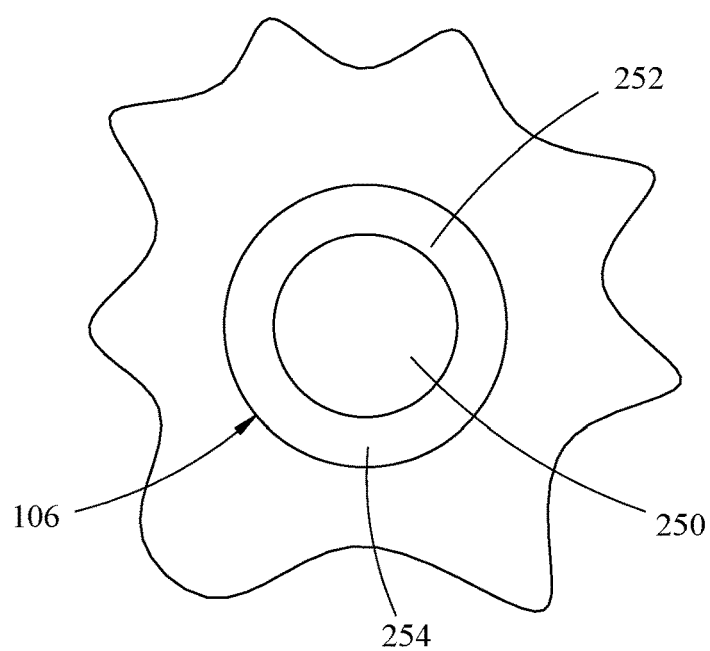
FIG. 14 shows in end view a probe through a body aperture in accordance with various embodiments.

FIG. 13 shows in a cross-sectional side view and FIG. 14 shows in an end view a probe 250 through the body aperture 106. The body aperture 106 effectively forms a body probe seal 252 with the probe 250 that has been inserted through the body aperture 106. Furthermore, a layer of lubricant 254 is typically lathered on the probe 250 before entry through the body aperture 106. The layer of lubricant 254 disposed between the body aperture 106 and the probe 250 further aids forming the body probe seal 252 between the body aperture 106 and the probe 250. The layer of lubricant 254 may be of any suitable type to reduce friction between the body aperture 106 and the probe 250

Figure 15:
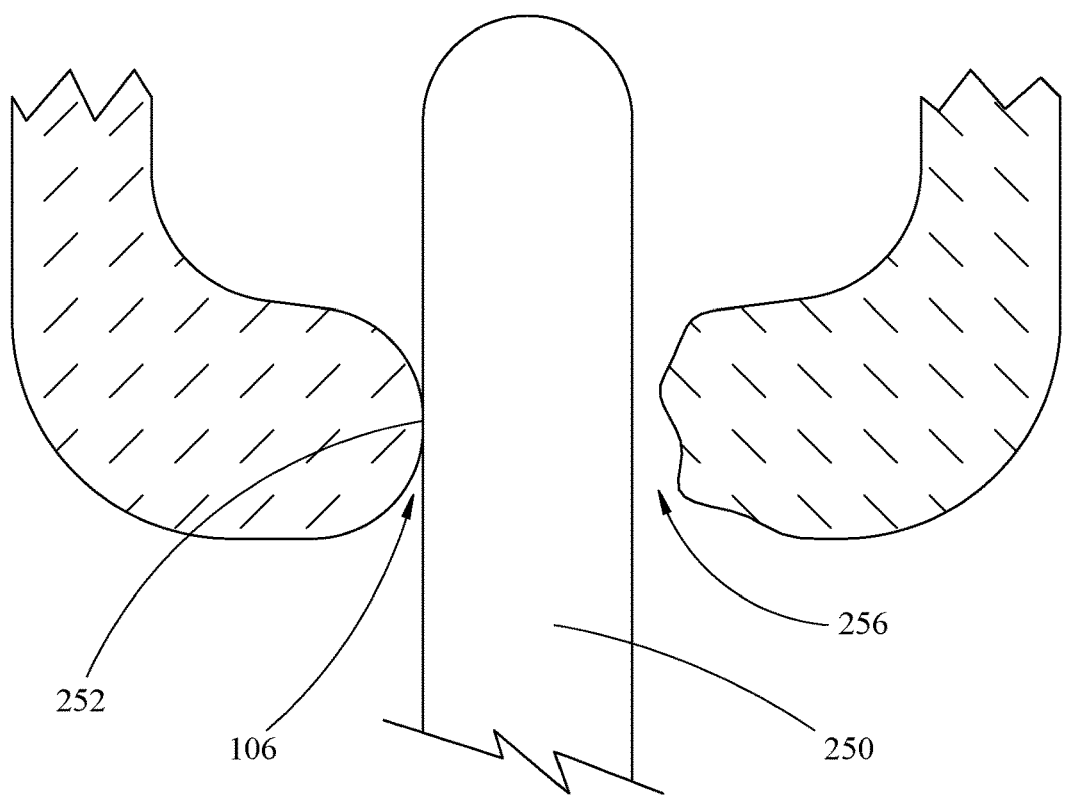
FIG. 15 shows in partial cross-section view a probe through a body aperture with an abnormality.
Figure 16:
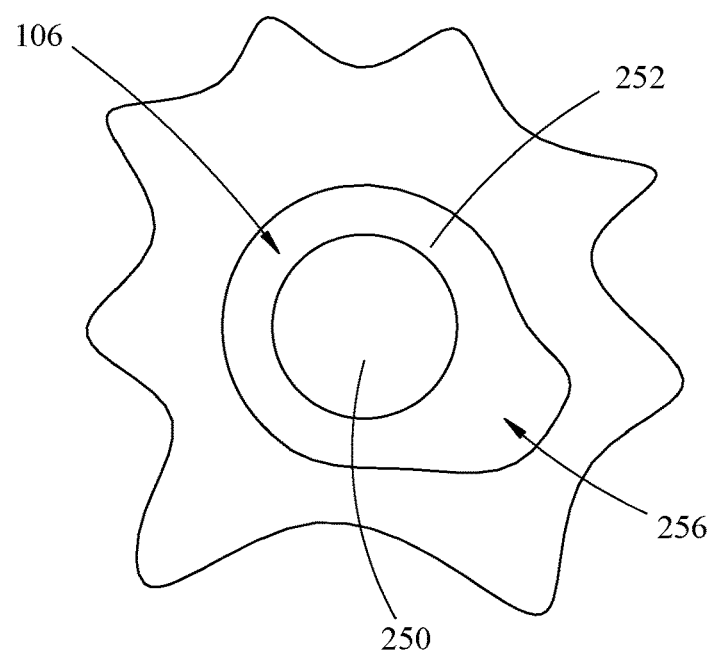
FIG. 16 shows in end view a probe through a body aperture with an abnormality.

FIG. 15 shows in a cross-sectional side view and FIG. 16 shows in an end view the probe 250 through the body aperture 106 with an abnormality 256. The body aperture 106 cannot effectively form the body probe seal 252 with the probe 250 that has been inserted through the body aperture 106 with the abnormality 256. For whatever reason, such as congenital malformation, abscess, previous abscess, muscle laxity, etc., the body aperture 106 does not effectively form the body probe seal 252 with the probe 250 through the body aperture 106.

Figure 17:
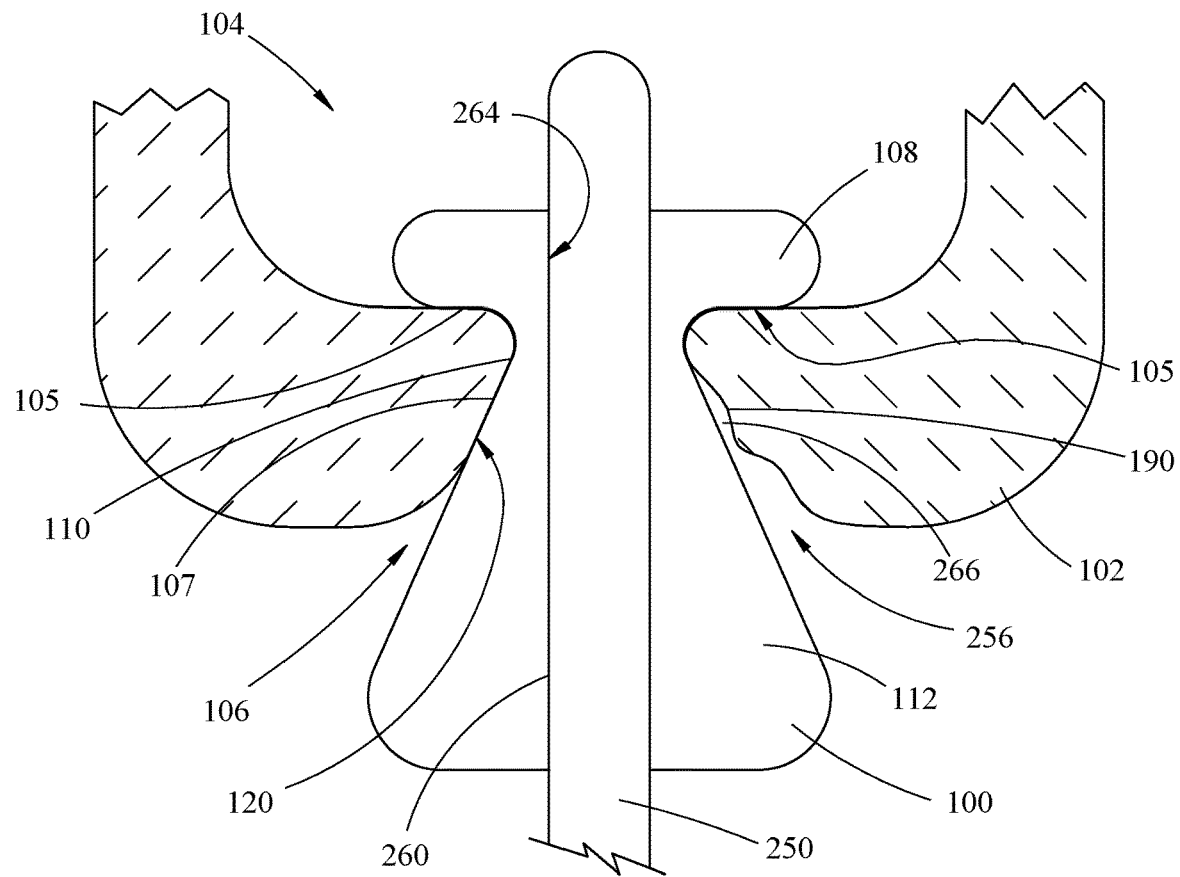
FIG. 17 shows in partial cross-section view a probe through a body aperture with an abnormality with the probe through an insufflation retention device in accordance with various embodiments.
Figure 18:
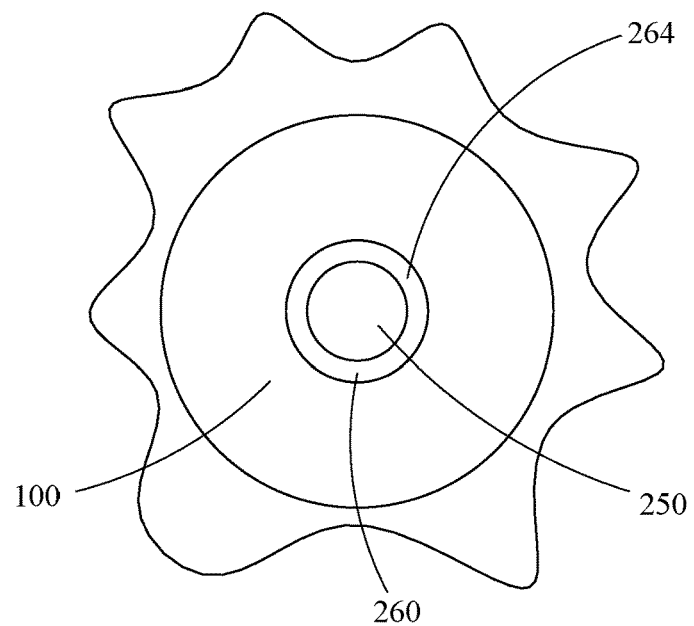
FIG. 18 shows in end view a probe through a body aperture within an abnormality with the probe through an insufflation retention device in accordance with various embodiments.
Figure 19:
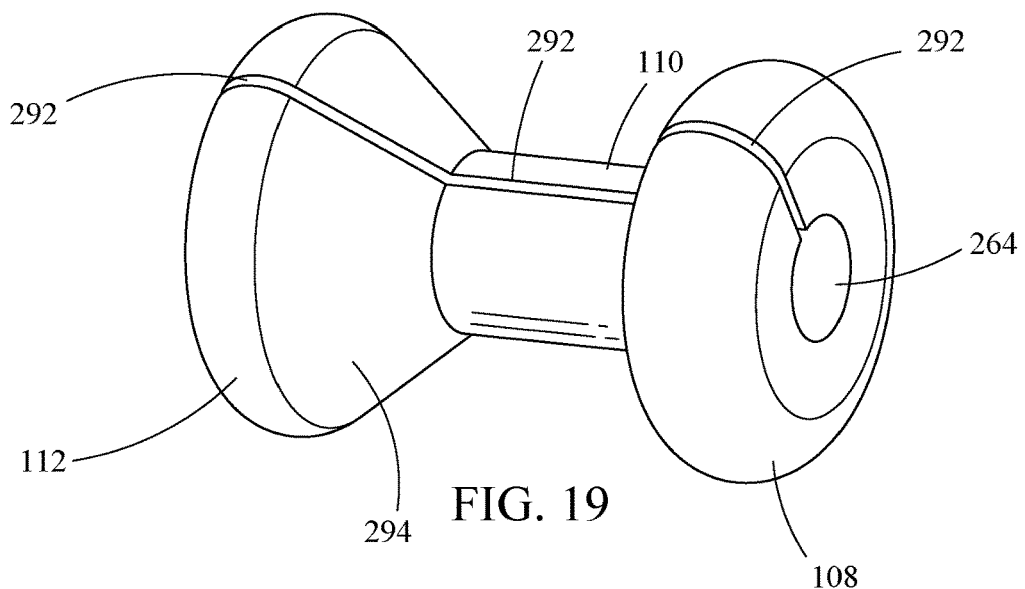
FIG. 19 shows in perspective view an insufflation retention device in accordance with various embodiments.
Figure 20:
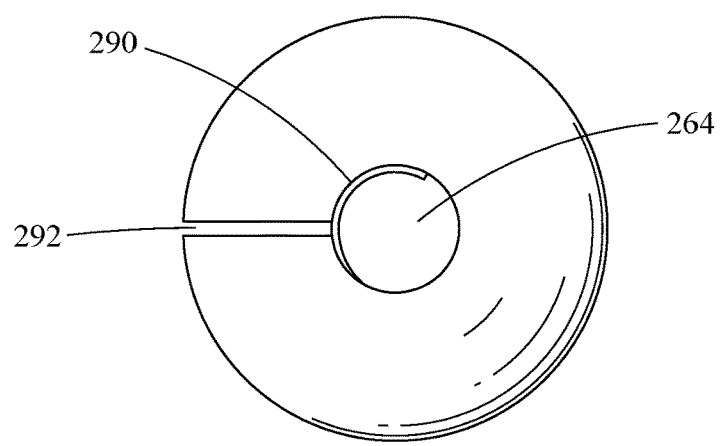
FIG. 20 shows in end view the insufflation retention device of FIG. 19 in accordance with various embodiments.
Figure 21:
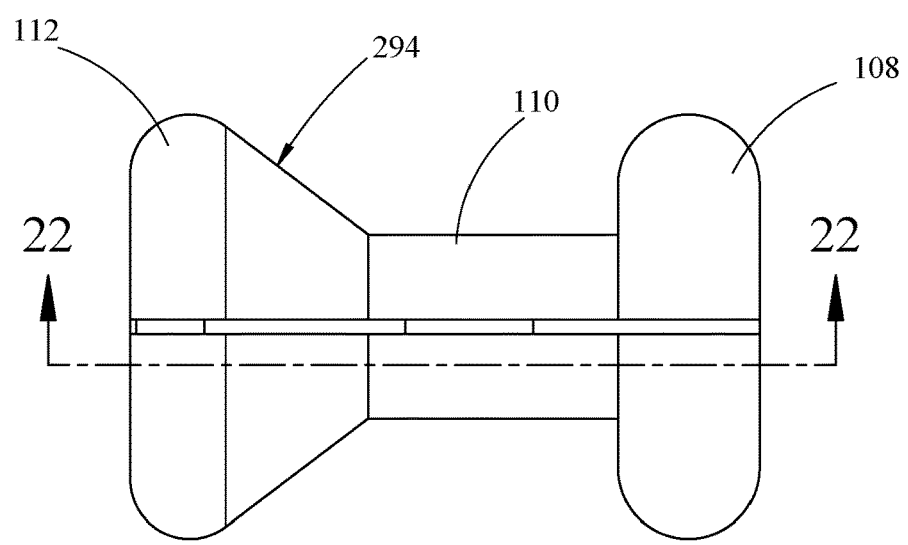
FIG. 21 shows in side view the insufflation retention device of FIG. 19 in accordance with various embodiments.
Figure 22:
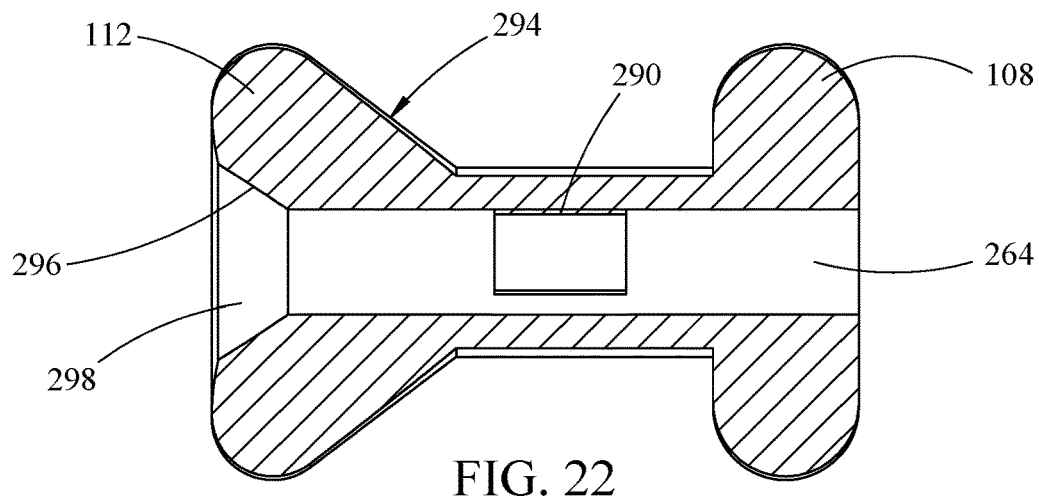
FIG. 22 shows in cross-section view the insufflation retention device of FIG. 22 in accordance with various embodiments.
Figure 23:
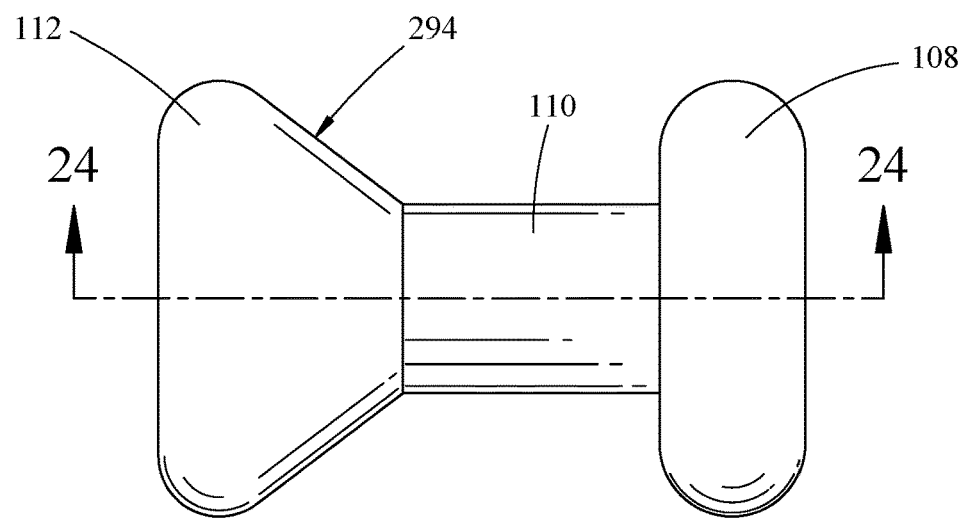
FIG. 23 shows in side view opposing side of the side of the insufflation device of FIG. 21 in accordance with various embodiments.
Figure 24:
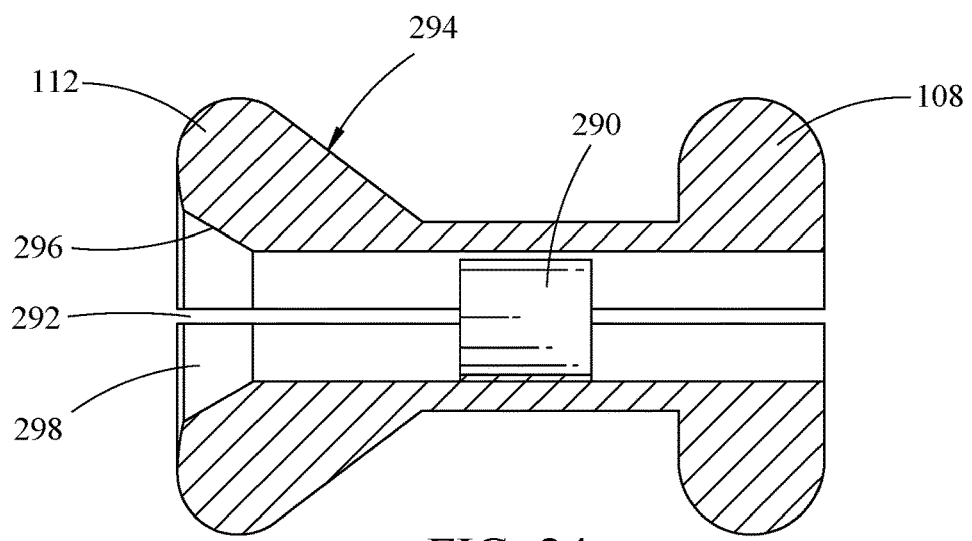
FIG. 24 shows in cross-section view the insufflation retention device of FIG. 23 in accordance with various embodiments.
Figure 25:
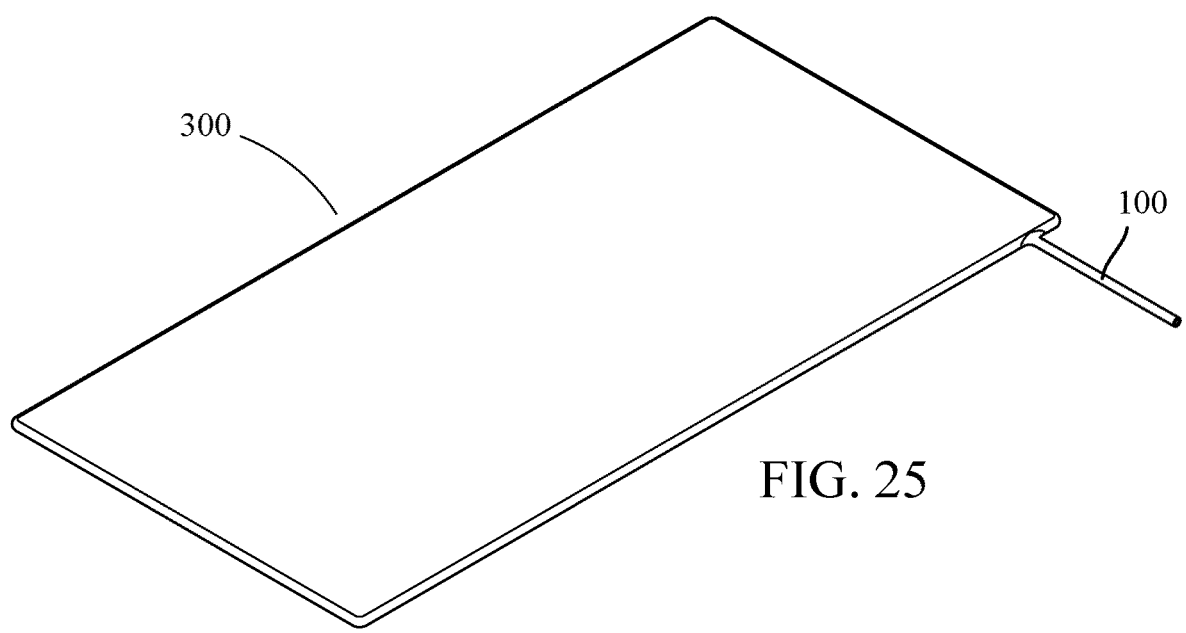
FIG. 25 shows perspective view of a passageway structure used in an insufflation retention device in accordance with various embodiments.
Figure 26:
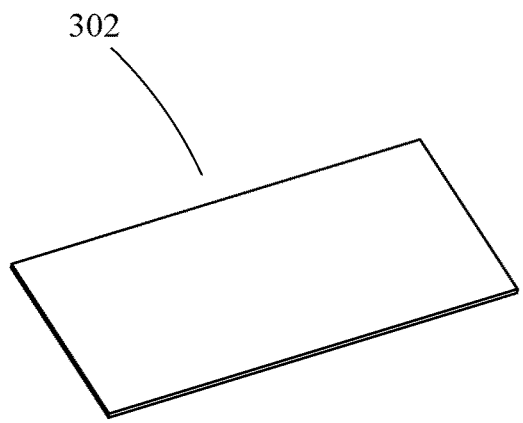
FIG. 26 shows a perspective view of an external compression member in an open state, wherein the external compression member is used in conjunction with the insufflation retention device of FIG. 25.

FIG. 17 shows in a cross-sectional side view and FIG. 18 shows in an end view a probe 250 through the body aperture 106 with the abnormality 256, and the probe 250 through the IRD 100 in accordance with various embodiments. Analogous to framing a window in a house, the IRD 100 can effectively form a seal with the body 102 to promote retention of the insufflation material in the body cavity 104. Furthermore, the IRD 100 can provide a sleeve of predetermined configuration and size responsive to the probe to effectively form another seal with the probe to further promote retention of the insufflation material in the body cavity 104.

Of course, the IRD 100 can be used with the probe 250 in the body aperture 106 without the presence of the abnormality 256. However, when the IRD 100 is used with the probe 250 in the body aperture 106 with the abnormality 256, the IRD 100 is configured to promote retention of the insufflation material inserted into the body cavity 104 for a time effective for operator performance of the diagnostic intervention, the therapeutic intervention, or both that is better than retention of the insufflation material could be achieved using the probe 250 without the IRD 100. A probe passageway seal 260, the body midportion seal 109, the body internal buttress seal 105, and the body internal buttress seal 105 may be configured to cooperate with the probe 250 to promote retention of the insufflation material inserted into the body cavity 104 for a time effective for operator performance of the diagnostic intervention, the therapeutic intervention, or both. On the other hand, the passageway 264 may be open without the probe 250 present in the passageway, such that the insufflation material may not be not retained in the body cavity 104.

The IRD 100 can effectively form seals, the body midportion seal 109 between the midportion 110 and the wall 120 of the body aperture 106, the body external buttress seal 107 between the external buttress 112 and the wall 120 of the body aperture 106, and the body internal buttress seal 105 between the internal buttress 108 and the body cavity 104 or the body 102, even in the presence of the abnormality 256. As shown in FIG. 17, the midportion 110 may blend or be operationally contiguous with the external buttress 112 to both function to inhibit advancement of the IRD 100 into the body cavity 104 during operation.

Further, the IRD 100 can effectively form the probe passageway seal 260 when the probe 250 is inserted in the IRD 100. A passageway 264 through the midportion 110 of the IRD 100 may be configured to form the probe passageway seal 260 between the probe 250 and the passageway 264. The passageway 264 extends past the first end 174 and past the second end 176 (see FIG. 5 and FIG. 6) of the IRD 100, so that the probe 250 extends all the way through the IRD 100.

In addition, the external surface 190 of the midportion 110 may be configured to provide a contour feature 266 to engage the abnormality 256 to provide an effective seal. Of course, the contour feature 266 may be a protrusion, indentation, or combination of both to engage the abnormality 256 to provide an effective seal. Further, the contour feature 266 may be formed from the external buttress 112 or both the midportion 110 and the external buttress 112. In addition, the internal buttress 108 may have a contour feature, as discussed previously shapes are contemplated depending on the need of the operator in view of the body 102 of a patient.

FIGS. 19-25 show various views of the IRD 100 in accordance with another embodiment. The IRD 100 may have the internal buttress 108 and the external buttress 112 with the midportion 110 therebetween. The IRD 100 may be made with a seam 292 that runs the length of the IRD 100 as shown, or a portion thereof. The seam 292 essentially may be a gap or split between surfaces of the material that is folded on itself to make the IRD 100. The seam 292 may not be present if the surfaces of the material that is folded on itself to make the IRD 100 abut each other. The external buttress 112 has a tapered surface 294 that is substantially conical to facilitate an effective seal with the body 102 (see FIG. 1).

An internal bias member 290 with biasing tension cooperates with a biasing tension of the rest of the IRD 100 to keep the IRD 100 closed during operation. The internal bias member 290 may be substantially flush with an interior of the IRD 100, or the internal bias member 290 may be substantially not flush with the interior of the IRD 100. On the other hand, the IRD 100 shown may be opened to wraparound the probe 250 when the probe 250 is in the body aperture 106, the body cavity 104, or both, and then the IRD may be inserted into and through the body aperture 106. The internal bias member 290 is configured for one-handed or two-handed operation.

An entry port 298 in the external buttress 112 may be configured to have a diameter wider than a diameter of the passageway 264, wherein the diameters are substantially parallel to each other. By having the diameter of the entry port 298 wider than the diameter of the passageway 264, the operator will have a larger target for insertion of the probe 250 into the passageway 264 then if the diameter of the entry port 298 was substantially the same size as the diameter of the passageway 264. The diameter of the passageway 264 may be configured and sized to fit closely around a diameter of the probe 250, so that the probe passageway seal between the passageway and the probe can be more easily achieved, and wherein again these diameters are substantially parallel to each other. There may be an internal taper 296 in the external buttress 112 so that the diameter of the entry port 298 can taper down to the smaller diameter of the passageway 264. While the internal taper 296 is shown as substantially linear resulting in a conical structure in FIG. 22, any suitable shape to facilitate the operator maneuvering the probe 250 into the passageway 264 is contemplated.

This embodiment is shown as a solid structure, which the IRD 100 may be if the internal buttress 108 is of a compressible material (e.g., foam by way of example and limitation), such that the internal buttress 108 may be pushed through the body aperture 106 in the contracted state and then once inside the body cavity 104, the internal buttress 108 may expand into the expanded state. Of course, this similar structure, such as with the entry port 298 having the internal tapered 296, may be present in conjunction with features from the other embodiments that include the internal buttress 108 that is expandable by the expansion material.

FIGS. 25-29 show various views of the IRD 100 in accordance with another embodiment. The internal buttress 108 and the external buttress 112 may be in fluid communication through the midportion 110, not shown, via what is effectively a rectangular balloon, also known herein as a passageway structure 300. The midportion 110 may be compressed by an external compression member 302 that essentially biases fluid within the passageway structure 300 towards the internal buttress 108 and the external buttress 112. The external compression member 302 may be contactingly adjacent an external surface of the passageway structure 300. The external compression member 302 in a closed position may or may not force substantially all the fluid, i.e., expansion material, from the midportion 110 in the IRD 100 that is ready for use by the operator. While the passageway structure 300 is indeed shown and conceived of as rectangular and in operation to be symmetrical, other appropriate sizes and dimensions are contemplated based on needs of the user in view of the body 102 of the patient.

Figure 27:
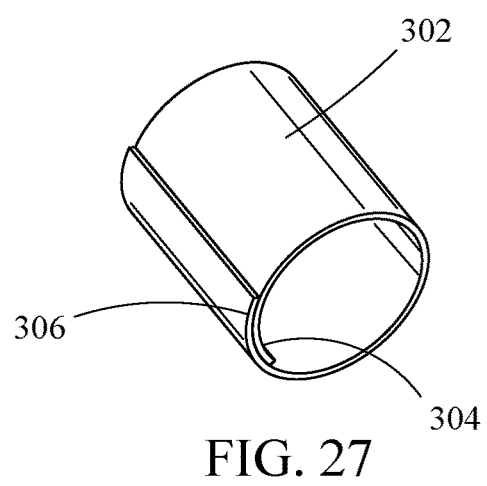
FIG. 27 shows a perspective view of the external compression member in a closed state used in conjunction with the insufflation retention device of FIG. 25.
Figure 28:
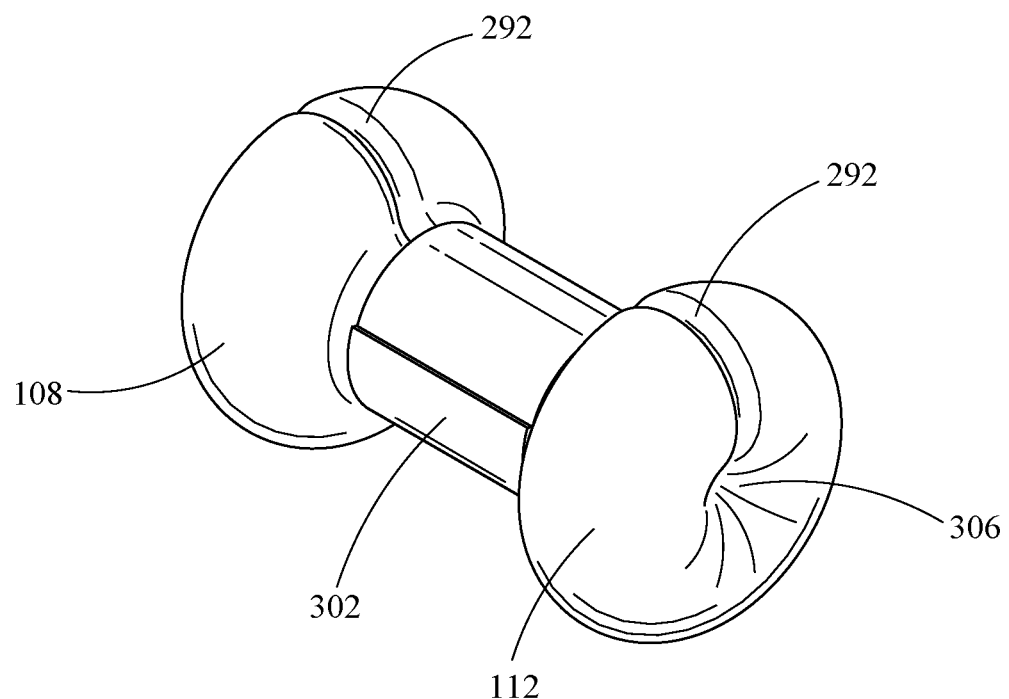
FIG. 28 shows a perspective view of the insufflation retention device of FIG. 25 in accordance with various embodiments.
Figure 29:
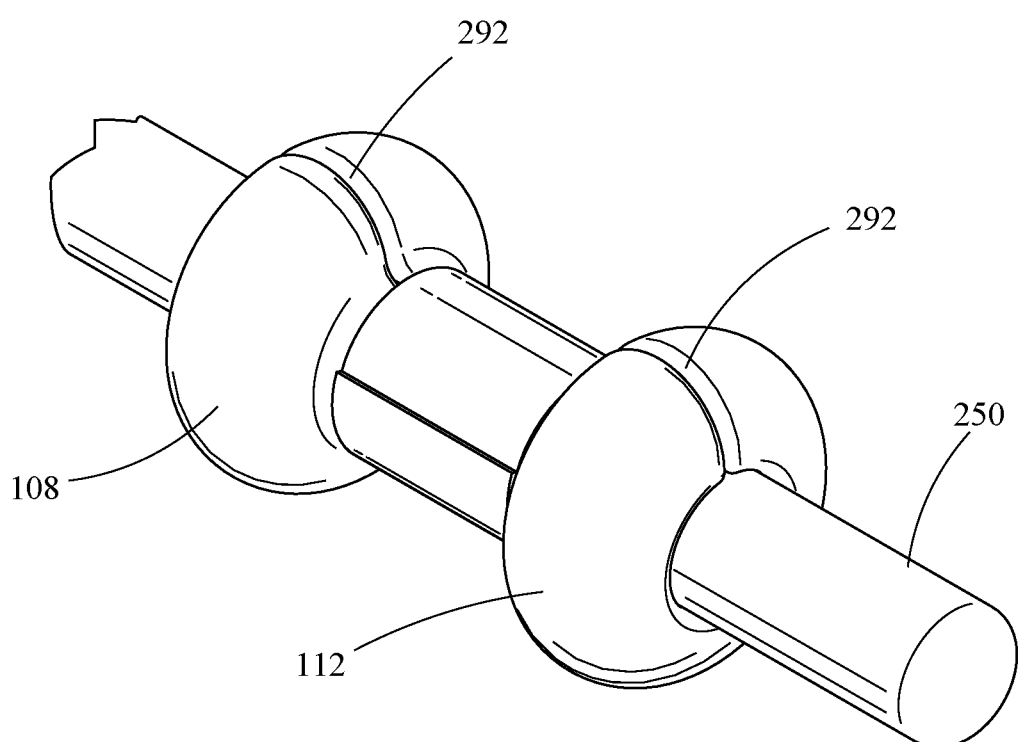
FIG. 29 shows a perspective view of the insufflation retention device of FIG. 25 with a probe through the passageway in accordance with various embodiments.

The external compression member 302 may have an internal bias member 304 that in the rolled configuration is internal to an external bias member 306 of the external compression member 302 in the closed position shown in FIGS. 27-29. Furthermore, while the external compression member 302 is shown to have an overlap with an external bias member 306 overlapping the internal bias member 304, the external compression member 302 may not overlap itself, just as the internal bias member 304 may not overlap itself. The external compression member 302 is configured for one-handed or two-handed operation from an open position, wherein the IRD 100 with the external compression member 302 in the open position may be positioned to encircle the probe 250 and in the closed position may be maintained around the probe 250.

While the external compression member 302 is shown external to the balloon that forms the internal buttress 108, the external buttress 112, and a portion of the midportion 110, it is fully contemplated that the external compression member 302 may be internal to the passageway structure 300.

Figure 30:
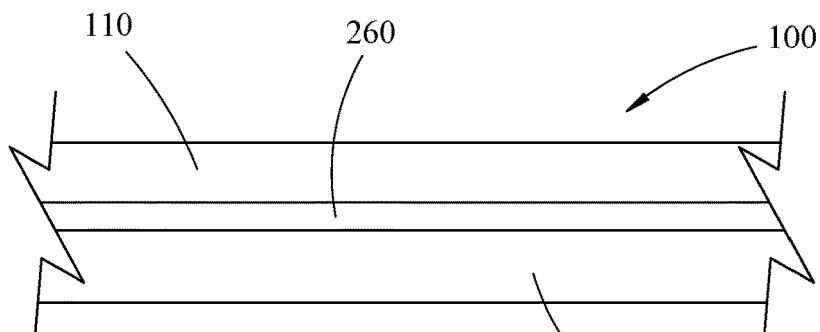
FIG. 30 shows in partial cross-section view an insufflation retention device with a probe in accordance with various embodiments.
Figure 31:
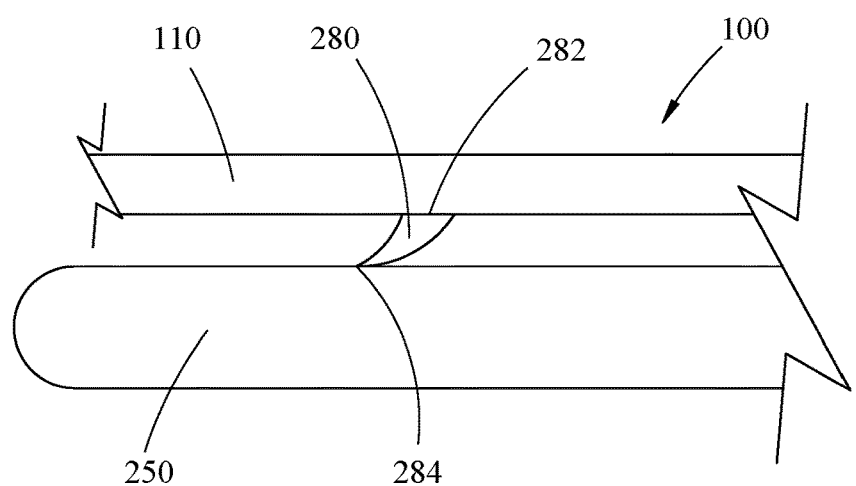
FIG. 31 shows in partial cross-section view and insufflation retention device with an O-ring type structure with a probe in accordance with various embodiments.
Figure 32:
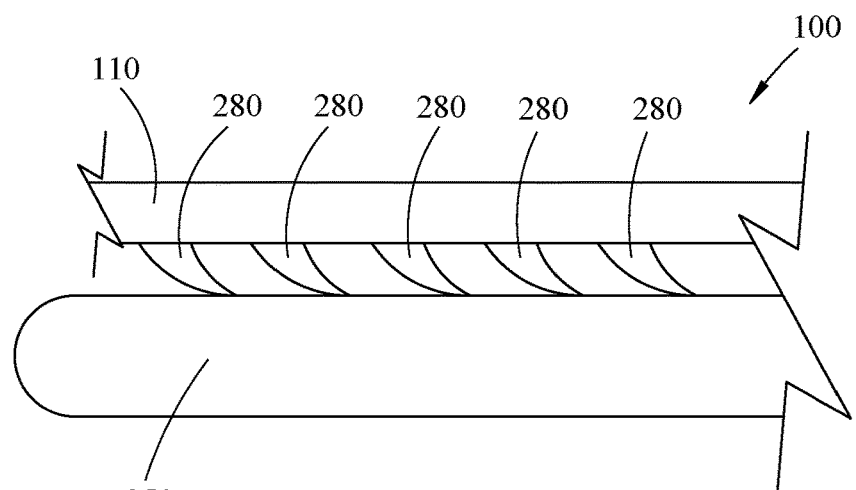
FIG. 32 shows in partial cross-section view and insufflation retention device with a plurality of O-ring type structures with a probe in accordance with various embodiments.

FIGS. 30-32 show cutaway side views of the IRD 100 with an O-ring type structure 280 or a plurality of O-ring type structure 280 in accordance with various embodiments. The IRD 100 may cooperate with the probe 250 to form the probe passageway seal 260 that is an effective seal between the IRD 100 and the probe 250. Further, the layer of lubricant 254 between the IRD 100 and the probe 250 may aid in or promote the effectiveness of the probe passageway seal 260 between the IRD 100 and the probe 250.

Further, the O-ring type structure 280 along the sleeve may further aid in promoting the seal between the IRD 100, e.g., the midportion 110, and the probe 250. The O-ring type structure 280 may be fixed to the sleeve at a first O-ring end 282 and mobile at an opposing, second O-ring end 284. The O-ring type structure 280 may be one of a plurality of O-rings type structures 280. While the O-ring type structure 280 may be rigid, there may be benefit in having the O-ring type structure 280 be flexible such that the opposing, second O-ring end 284 is dragged internally towards the body cavity 104 when the probe 250 is advanced and the opposing, second O-ring end 284 is dragged externally away from the body cavity 104 when the probe 250 is retracted.

As shown throughout the disclosure in the various embodiments, the internal buttress 108 and the external buttress 112 in some embodiments are not configured to engage the probe 250 and therefore the internal buttress 108 and the external buttress 112 may not contribute to the seal between the IRD 100 and the probe 250. In other embodiments, the internal buttress 108 and the external buttress 112 are configured to engage the probe 250 and therefore the internal buttress 108 and the external buttress 112 may contribute to the seal between the IRD 100 and the probe 250. Whether the internal buttress 108 and the external buttress 112 engage the probe 250, the internal buttress 108 and the external buttress 112 may contribute to the seal between the IRD 100 and the body 102, such as the body cavity 104, the body aperture 106, and the wall 120 of the body aperture 106.

Of course, care is taken to optimize the contact of the internal buttress 108, the external buttress 112, and other portions of the IRD 100 with the body 102, the body cavity 104, and the body aperture 106, and other aspects of a patient to minimize the risk for pressure necrosis or other untoward side effects from using the IRD 100. This care may be implemented by having a predetermined volume for the expansion material, which will in turn establish a predetermined pressure that the internal buttress 108, the external buttress 112, etc. of the IRD 100 exerts on the body 102, the body cavity 104, the body aperture 106, etc.

A method of using the IRD 100 may comprise the following steps. At the first step, the IRD 100 is inserted through the body aperture 106 of the body 102 into the body cavity 104 of the body 102. At the second step, the insufflation material is injected into the body cavity 104. At the third step, a user uses a probe to perform a diagnostic intervention, a therapeutic intervention, or both a diagnostic intervention and a therapeutic intervention. Further steps are contemplated. For example, and not by way of limitation, the probe may be inserted through the body aperture 106 before, after, or in conjunction with the IRD being inserted through the body aperture 106.

It is to be understood that even though numerous characteristics and advantages of various embodiments of the present disclosure have been set forth in the foregoing description, together with details of the structure and function of various embodiments of the disclosure, this detailed description is illustrative only, and changes may be made in detail, especially in matters of structure and arrangements of parts within the principles of the present disclosure to the full extent indicated by the broad general meaning of the terms in which the appended claims are expressed.

What is claimed is:

1. An apparatus comprising:
an internal buttress configured to inhibit removal of the internal buttress from a body cavity through a body aperture of a body of a patient;
an external buttress coupled to the internal buttress, the external buttress configured to inhibit entry of the external buttress into the body cavity through the body aperture;
a passageway extending through the internal buttress and the external buttress that is configured for passage of a probe into contacting engagement with the body cavity; and a seam extends from the internal buttress to the external buttress and which allows the apparatus to be opened and wrapped around the probe,
wherein a size of the internal buttress is increased from an unexpanded state to an expanded state through introduction of an expansion material.

2. The apparatus of claim 1, wherein an interior surface of the passageway is substantially circular through the internal buttress to the external buttress.

3. The apparatus of claim 1, further comprising:
an entry port in the external buttress, wherein a diameter of the entry port is wider than a diameter of the passageway, wherein the diameter of the entry port and the diameter of the passageway are substantially parallel to each other.

4. The apparatus of claim 1, wherein the external buttress does not have an unexpanded state.

5. An apparatus for insertion into a patient for use with a probe configured to perform diagnostic intervention, therapeutic intervention, or both, said apparatus comprising:
an internal buttress, wherein in a contracted state the internal buttress is configured for insertion through a body aperture of a body into a body cavity of the body of the patient and in an expanded state the internal buttress is configured to inhibit removal of the internal buttress from the body cavity through the body aperture, wherein the internal buttress is configured to form a body internal buttress seal between the body cavity and the internal buttress;
an external buttress configured to inhibit advancement of the external buttress through the body aperture into the body cavity, the external buttress is configured to form a body external buttress seal between the body and the external buttress;
a midportion disposed between the internal buttress and the external buttress, the midportion is configured to form a body midportion seal between the body aperture and the midportion;
a passageway through the midportion configured for passage of the probe into the body cavity, wherein the passageway is configured to form a probe passageway seal between the probe and the passageway, and wherein the probe passageway seal, the body midportion seal, the body internal buttress seal, and the body external buttress seal are configured to promote retention of an insufflation material inserted into the body cavity for a time effective for operator performance of the diagnostic intervention, the therapeutic intervention, or both, wherein an interior surface of the midportion is substantially circular so that the midportion is configured to be relatively free to rotate about the probe, and the interior surface is disposed symmetrically within the midportion; and a seam that runs a length of the apparatus and which allows the apparatus to be opened and wrapped around the probe.

6. The apparatus of claim 5, wherein the external buttress is configured to have an entry port with a diameter of the entry port wider than a diameter of the passageway, wherein the diameter of the entry port and the diameter of the passageway are substantially parallel to each other.

7. The apparatus of claim 5, wherein the external buttress is configured to have an entry port that is tapered from a larger opening at an end of the external buttress to a smaller opening towards the midportion.

8. The apparatus of claim 5, wherein the internal buttress is configured to not engage the probe and does not contribute to a probe internal buttress seal.

9. The apparatus of claim 5, wherein an interior surface of the passageway is substantially circular through the internal buttress to the external buttress.

10. The apparatus of claim 5, wherein the external buttress does not have an unexpanded state.

11. The apparatus of claim 5, wherein a size of the internal buttress is increased from an unexpanded state to an expanded state through introduction of an expansion material.

12. An insufflation retention device for insertion into a patient for use with a probe configured to perform diagnostic intervention, therapeutic intervention or both, said insufflation retention device comprising:

an internal buttress configured to inhibit removal of the internal buttress from a body cavity through a body aperture of a body, wherein a size of the internal buttress is increased from an unexpanded state to an expanded state through introduction of an expansion material;

an external buttress coupled to the internal buttress, the external buttress configured to inhibit entry of the external buttress into the body cavity through the body aperture;

a midportion disposed between the internal buttress and the external buttress, the midportion is configured to form a probe passageway seal between the probe and the midportion;

a passageway extending through the internal buttress, the midportion, and the external buttress, the passageway is disposed symmetrically within the midportion with an interior surface of the passageway that is substantially circular so the passageway is able to freely rotate about the probe, and the passageway is configured to be open without the probe present in the passageway so an insufflation material introduced into the body cavity is not retained in the body cavity, and configured to be closed by the probe passageway seal when the probe is present in the passageway so the insufflation material introduced into the body cavity is retained in the body cavity; and a seam that runs from the internal buttress to the external buttress and which allows the insufflation retention device to be opened and wrapped around the probe.

13. The insufflation retention device of claim 12, wherein the internal buttress is configured to not engage the probe and the internal buttress is not configured to contribute to a seal on the probe.

14. The insufflation retention device of claim 12, wherein the external buttress is configured to not engage the probe and the external buttress is not configured to contribute to a seal on the probe.

15. The insufflation retention device of claim 12, wherein an exterior periphery of the internal buttress is configured to be expandable from an unexpanded configuration to an expanded configuration, and an interior periphery of the internal buttress is configured to be relatively rigid in comparison to the exterior periphery.

16. The insufflation retention device of claim 12, wherein the insufflation retention device is configured to have an open configuration wherein the internal buttress, the midportion, and the external buttress are configured to be positioned around the probe that is in the body aperture, and a closed configuration wherein the internal buttress, the midportion, and the external buttress are configured to wrap around the probe to retain the insufflation material in the body cavity.

17. The insufflation retention device of claim 12, wherein the external buttress does not have an unexpanded configuration.

18. An insufflation retention device comprising:

an internal buttress configured to inhibit removal of the internal buttress from a body cavity through a body aperture of a body, wherein a size of the internal buttress is increased from an unexpanded state to an expanded state through introduction of an expansion material;

a passageway extending through the internal buttress that is configured for passage of a probe into contacting engagement with the body cavity; and a gap in the internal buttress, wherein the gap extends from the passageway through the internal buttress to an exterior periphery of the internal buttress.

19. The insufflation retention device of claim 18, further comprising:

an external buttress coupled to the internal buttress, the external buttress configured to inhibit entry of the external buttress into the body cavity through the body aperture; and an entry port in the external buttress, wherein a diameter of the entry port is wider than a diameter of the passageway, wherein the diameter of the entry port and the diameter of the passageway are substantially parallel to each other.

20. The insufflation retention device of claim 19, further comprising:

a midportion between the internal buttress and the external buttress, wherein the midportion comprises a body that includes an expansion material conduit configured to introduce the expansion material into an internal cavity of the internal buttress.

21. The insufflation retention device of claim 18, further comprising:

an external buttress coupled to the internal buttress, the external buttress configured to inhibit entry of the external buttress into the body cavity through the body aperture, and wherein the external buttress does not have an unexpanded configuration.

22. The insufflation retention device of claim 18, wherein the internal buttress in the expanded state is configured to inhibit removal of the internal buttress from the body cavity through the body aperture, and the internal buttress in the unexpanded state is configured to promote entry of the internal buttress into the body cavity through the body aperture.

23. The insufflation retention device of claim 22, wherein the internal buttress is expanded with insertion of the expansion material to inhibit removal of the internal buttress from the body cavity through the body aperture, and the internal buttress is contracted with removal of the expansion material to facilitate removal of the internal buttress from the body cavity through the body aperture.

24. The insufflation retention device of claim 18, wherein the internal buttress is expanded with insertion of the expansion material to inhibit removal of the internal buttress from the body cavity through the body aperture, and the internal buttress is contracted with removal of the expansion material to facilitate removal of the internal buttress from the body cavity through the body aperture.

25. The insufflation retention device of claim 18, further comprising:
    a first body portion coupled to a second body portion via a hinge portion at a first hinged side of the first body portion and a second hinged side of the second body portion.

26. The insufflation retention device of claim 25, wherein the hinge portion is configured to allow an operator to take the insufflation retention device from an open configuration to a closed configuration.

27. The insufflation retention device of claim 18, further comprising:
    a first body portion coupled to a second body portion via a flexible member at a first hinged side of the first body portion and a second hinged side of the second body portion.

28. The insufflation retention device of claim 27, wherein the flexible member is configured to allow an operator to take the insufflation retention device from an open configuration to a closed configuration.

29. The insufflation retention device of claim 18, further comprising:
    an internal buttress portion coupled to the internal buttress, wherein the internal buttress portion has a bias to a closed state to form a sleeve that is sized and dimensioned to fit the probe.

* * * * *